(12) United States Patent
Meltzer et al.

(10) Patent No.: US 7,439,264 B2
(45) Date of Patent: Oct. 21, 2008

(54) THERAPEUTIC COMPOUNDS

(75) Inventors: Peter C. Meltzer, Lexington, MA (US);
Bertha K. Madras, Newton, MA (US);
Paul Blundell, Winchester, MA (US);
Shanghao Liu, Andover, MA (US)

(73) Assignees: President and Fellows of Harvard College, Cambridge, MA (US);
Organix, Inc., Woburn, MA (US)

( * ) Notice: Subject to any disclaimer, the term of this patent is extended or adjusted under 35 U.S.C. 154(b) by 13 days.

(21) Appl. No.: 10/364,028

(22) Filed: Feb. 10, 2003

(65) Prior Publication Data

US 2003/0232827 A1 Dec. 18, 2003

Related U.S. Application Data

(60) Provisional application No. 60/355,111, filed on Feb. 8, 2002, provisional application No. 60/367,400, filed on Mar. 25, 2002.

(51) Int. Cl.
*A61K 31/38* (2006.01)
*A61K 31/336* (2006.01)
*C07D 313/02* (2006.01)
*C07D 495/00* (2006.01)

(52) U.S. Cl. .................... 514/431; 514/450; 549/9; 549/346

(58) Field of Classification Search ............ 514/431, 514/450; 549/9, 346
See application file for complete search history.

(56) References Cited

U.S. PATENT DOCUMENTS 5,948,933 A    9/1999  Meltzer et al. .............. 558/426
6,525,206 B1   2/2003  Meltzer et al. .............. 549/427
6,531,483 B1   3/2003  Kuhar et al. ................ 514/304

FOREIGN PATENT DOCUMENTS

| | | |
|---|---|---|
| DE | 202 03 103 U 1 | 8/2002 |
| EP | 1 051 980 A2 | 11/2000 |
| WO | WO 01/89524 A1 | 11/2001 |
| WO | WO 02/32842 A2 | 4/2002 |

OTHER PUBLICATIONS

Zou et al., J. Med. Chem. (2001), vol. 44(25), pp. 4453-4461.*
Meltzer et al., Biorg. Med. Chem. Letters (1999), vol. 9(6), pp. 857-862.*
Koziowski et al., J. Med. Chem. (1995), vol. 38(16), pp. 3086-3093.*
P. Meltzer, et al., *"Design and Synthesis of an Irreversible Dopamine-Sparing Cocaine Antagonist,"* Bioorganic & Medicinal Chemistry, vol. 10, No. 11, (Nov. 2002), pp. 3583-3591; XP-002313676.
Mu-Fa Zou, et al. "Novel Tropane-Based Irreversible Ligands for the Dopamine Transporter", J. Med. Chem. 2001, 44, 4453-4461.

* cited by examiner

*Primary Examiner*—Taofiq A Solola
(74) *Attorney, Agent, or Firm*—Edwards Angell Palmer & Dodge LLP; George W. Neuner; Mark D. Russett

(57) ABSTRACT

This invention to antagonists that inhibit transporters and receptors. The invention also relates to partial inhibitors of transporters and receptors that allow partial transport or partial binding of a compound to the transporter or receptor. The invention also relates to compounds that differentially prevent transport or binding through a transporter or to a receptor. The invention also relates to the use of these compounds for treating certain diseases and disorders.

20 Claims, 6 Drawing Sheets

O-2338

O-2190

O-2582

O-2774

O-2775

O-2727

O-2728

O-2729

O-2730

O-2731

O-2732

O-2741

THERAPEUTIC COMPOUNDS

RELATED APPLICATION(S)

This application claims priority to U.S. Provisional Patent Application Ser. No. 60/355,111, filed Feb. 8, 2002, and U.S. Provisional Patent Application Ser. No. 60/367,400, filed Mar. 25, 2002, the entire teachings of which are incorporated herein by reference.

STATEMENT OF GOVERNMENT SUPPORT

This invention was made with government support under Grant Nos. DA11542, DA7-8081 DA11558, DA06303, and DA00304, each of which was awarded by National Institute On Drug Abuse (NIDA), and RR00168, which is funded by the National Center for Research Resources (NCRR). The government has certain rights in the invention.

FIELD OF THE INVENTION

This invention is in the general field of antagonists that inhibit transporters and receptors. The invention also relates to partial inhibitors of transporters and receptors that allow partial transport or partial binding of a compound to a receptor. The invention also relates to compounds that differentially prevent transport or binding through a transporter or to a receptor. The invention also relates to the use of these compounds for treating certain diseases and disorders.

BACKGROUND OF THE INVENTION

Various medical interventions involve inhibiting monoamine transport and/or inhibiting binding to monoamine receptors. One example concerns cocaine, a potent stimulant of the mammalian central nervous system. Cocaine's reinforcing and stimulant properties have been associated with its propensity to bind to the dopamine. transporter (DAT). Such binding causes an inhibition of dopamine (DA) transport and a subsequent increase in concentration of extracellular DA for activation of postsynaptic receptors. Cocaine inhibition of dopamine transport and the resulting surge in extracellular dopamine levels is thought to be a major contributor to the stimulant and reinforcing properties of cocaine.

One approach considered for treating cocaine dependence involves cocaine congeners that prevent cocaine binding to the dopamine transporter. A significant problem associated with the use of cocaine congeners is that (like cocaine) the congeners tend to block dopamine reuptake and thereby elevate extracellular dopamine levels. In that way, congeners may produce reinforcing effects by the same mechanism that cocaine does, with a consequent potential for abuse. Madras et al., J. Pharmacol, Exp. Ther., 251:131-141 (1989); Bergman et al., J. Pharmacol, Ther., 251:150-155 (1989).

It has therefore been a goal of research to discover a molecule that can inhibit cocaine binding to the DAT but continue to allow DA transport by the DAT. While the cocaine inhibitor would still bind to the DAT, it would affect the rate of reuptake of DA by this transporter to a lesser extent. In this manner, the concentration of DA in the synapse would remain at normal physiological levels. It would be useful to discover molecules that can inhibit binding of certain compounds to the transporter or receptor but continue to allow transport of desired ligands through the transporter.

Similarly, it would be useful to block entry of other types of addictive drugs, e.g. MDMA, methamphetamine, amphetamine, that are similar to but not identical with the natural monoamine transmitters to the cell interior without blocking serotonin, norepinephrine or dopamine transport.

In these instances, it would be desirable to have an antagonist that is not simply a molecule that will inhibit binding of the drug at the transporter, but more importantly, it will permit transport of synaptic DA to the presynaptic neuron.

Most antagonists bind the transporter or receptor and prevent the binding or transport of all other molecules or substrates, even those that are. desirable to be transported. Thus, it would be useful to have compounds that prevent the transport or binding of certain compounds to the transporter or receptor but allow others to pass through.

There are also instances where it would be useful to have partial blockage of transporters or receptors to decrease the transport of substances whose build up results in negative effects. For example, Parkinsonism can be caused by entry of a neural toxin called MPP+ (1-methyl-4-phenylpyridine) into dopamine cells in the brain. It would be useful to have a mechanism that impedes the entry of MPP+ or other dopamine neuron toxins into dopamine cells without blocking access of dopamine. Such a compound can be used as a neuroprotective agent, if a neurotoxin is involved and uses the dopamine transporter.

For the treatment of schizophrenia, partial agonists have been assessed that target dopamine receptors. In contrast, agonists presently used, e.g. D2-D3 dopamine receptor antagonists, produce negative side effects such as muscle stiffness and unintended movements, as well as an inability to still restless legs. Presently used antipsychotic drugs act by modulating dopamine and other neurotransmitter signaling systems in the brain. The basic mechanism of conventional antipsychotic drugs is to reduce the effects of dopamine. This is achieved by drug blockade of D2 receptors on the dopamine-responding cells. By analogy to the DAT, partial blockade at the dopamine receptors by a drug may be useful to treat schizophrenia but allow partial use of dopamine that is necessary for normal cell function.

Selective serotonin re-uptake inhibitors (SSRIs) are a group of drugs used to treat major depression, dysthymia, panic disorder, obsessive-compulsive disorder, eating disorders, and premenstrual dysphoric disorder. They include citalopram (Cipramil), fluoxetine (Prozac), fluvoxamine (Faverin), paroxetine (Seroxat), and sertraline (Lustral). In these diseases, e.g., depression, the levels of neurotransmission in the brain are disturbed. SSRIs elevate serotonin levels, by reducing its uptake through serotonin transporters (SERT) into brain cells. People who take SSRIs may experience side effects including gastrointestinal disturbances, headache, sedation, insomnia, activation, weight gain, impaired memory, excessive perspiration, paresthesia, and sexual dysfunction. The side effects are due in part to inhibition of sertonin transport in the brain.

Tricyclic antidepressants, (commonly called TCAs) are also prescribed for depression. Examples of TCAs are: imipramine (Tofranil), amitriptyline (Elavil) and nortriptyline (Pamelor). TCAs work by raising the levels of serotonin and norepinephrine in the brain by slowing the rate of reuptake, or reabsorption, by nerve cells. TCAs tend to have more unpleasant side effects than the newer antidepressants such as SSRIs. The side effects of TCAs vary with the specific medication taken and the individual. Some typical side effects include drowsiness, anxiety, restlessness, dry mouth, constipation, urinary retention, difficulty urinating, cognitive and memory difficulties, weight gain, increased sweating, dizziness, decrease in sexual ability and desire, muscle twitches, fatigue, weakness, nausea, increased heart beats, irregular heart rhythms (very rare). Thus, it would be useful to have a mechanism to reduce certain side effects of tricyclic antidepressants and SSRI's, e.g., by allowing partial transport of serotonin that is necessary for normal cell function.

Thus, it would be useful to have a general mechanism by which transport of endogenous and exogenous ligands through certain transporters can be controlled.

SUMMARY OF THE INVENTION

The present invention relates to compounds that inhibit undesired binding to the transporter or receptor of interest while sparing natural transport to a significant but varying degree.

The invention thus features a family of molecules that comprise a ligand for a monoamine transporter or a receptor, and an acceptor moiety, containing a barb, that tightly binds a site at a monoamine transporter or a receptor. The compounds may include DAT-specific tropane moieties which serve to target the desired biological structure. The acceptor moiety is selected from any group which is capable of tight binding to the biological target and includes, but is not limited to, a nucleophile acceptor such as an epoxide or a double bond, an electrophile acceptor or a radical acceptor.

The invention thus relates to compounds comprising a) a ligand for a transporter or receptor and b) a linker-acceptor moiety (LAM) connected to the ligand, wherein the LAM comprises 1) an acceptor moiety that covalently binds the transporter or receptor and 2) a linker which attaches the ligand to the acceptor moiety. In the compounds of the present invention, the linker comprises a cleavable bond, cleavage of which produces at least two components: (1) a barb that remains attached to the transporter or receptor and (2) the ligand, wherein the ligand is released from the compound. Preferably the cleavable bond is an ether, thioether or amino or bond. In certain embodiments, the acceptor moiety is a nucleophile acceptor. In preferred embodiments the acceptor moiety is an epoxide, in other embodiments the acceptor moiety is an alkenyl moiety.

More specifically the present invention relates to compounds that act as neurotransmitter sparing antagonists of substances acting at monoamine transporters or receptors. For example, the present invention relates to compounds that inhibit undesired binding to the transporter (e.g. DAT), while sparing natural monoamine transport (e.g., dopamine reuptake) to a varying degree. For example these compounds differentially affect cocaine-DAT binding on the one hand and DAT-based dopamine transport on the other hand. In that way, the compounds may reduce or avoid reinforcing effects and the possibility of abuse that often characterize inhibitors of cocaine binding to its target.

In preferred embodiments, the transporter is a monoamine transporter and the acceptor moiety binds the monoamine transporter. Preferably the ligand of the compound is a ligand for at least one transporter selected from the dopamine, norepinephrine and serotonin transporters. In other embodiments, the ligand is a ligand for at least one receptor selected from the dopamine, norepinephrine and serotonin receptors. In certain embodiments, the monoamine transporter is DAT. In preferred embodiments, the ligand comprises a tropane and the monoamine transporter is the dopamine transporter. In other embodiments, the ligand comprises a tropane moiety and the monoamine transporter is the serotonin transporter.

In certain preferred compounds of the present invention, the compounds comprise a ligand having the following Formula 1

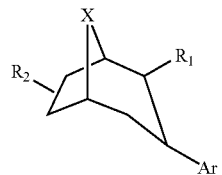

Where:
the 2-, 3-, 6-, or 7-positions are α or β;
the compounds are racemic or 1R- or 1S-configured;
X=O, $NR_3$, $NR_9$, $CHR_3$, $CHR_1$, $CH_2$, $CHW_1$, $CW_1W_1$, CO, S, SO, $SO_2$, $NSO_2R_3$, $NSO_2R_1$, or $CX_2W$, with the N, C, O or S atom being a member of the ring;
Ar=Phenyl or 1-naphththyl or 2-naphthyl, unsubstituted or substituted with one or more group selected from: —H; —Br; —Cl; —I; —F; —OH; —$CH_3$; —$CF_3$; —$NO_2$; —$NH_2$; —CN; —$NHCOCH_3$, —$C(CH_3)_3$, —$C(CH_2)$ $CH_3$, $(CH_2)_qCH_3$, where q=0-6; —$COCH_3$; alkyl; alkenyl; alkynyl; allyl; isopropyl; isobutyl; wherein each substitutent can be at the 2, 3 and/or 4 position of the ring;
W or $X_2$=H, OH, $OCH_3$, OAc, $OCOR_4$, $CH_3$, $(CH_2)_nCH_3$, $R_4$;
$W_1$=H, Br, Cl, I, F, OH, $OCH_3$, $CF_3$, $NO_2$, $NH_2$, CN, $NHCOCH_3$, $N(CH_3)_2$, $(CH_2)_nCH_3$, $COCH_3$, or $C(CH_3)_3$;
$X_1$=$NR_3$, $CH_2$, $CHR_4$, $CR_3R_4$, CO, O, S; SO, $SO_2$, $NSO_2R_1$, or $NSO_2R_3$;
$R_1$=H, $COOCH_3$, $COOR_4$, $COR_4$, $CH_2OH$, $(CH_2)_nOH$, $(CH_2)_nOR_4$, $CR_3$=$NOR_3$, CH=$NR_3$;
$R_2$=H, OH, $OCOR_4$, $OCOR_5$, where $R_5$ is not F, Cl;
$R_3$=H, $CH_3$, $CH_2Ar$, $(CH_2)_nAr$, Ar, lower alkyl, lower alkenyl or lower alkynyl; $CH_2CH$=CHZ, $(CH_2)_nOH$, $(CH_2)_nOR_4$, CH=CHZ; $CH_2$J-Maleimide, $CH_2$JN-Maleimide where J=$CH_2$ or O; $(CH_2)_nOCOCH_3$; $(CH_2)_nOCOCH_2OCH_3$; $(CH_2)_n$-morpholine; $(CH_2)_n$-piperidine; $(CH_2)_n$-piperazine;
$R_4$=$CH_3$, $CH_2CH_3$, alkyl, alkenyl, alkynyl, allyl, isopropyl, isobutyl;
$R_9$=H, $COOCH_3$, $COOR_4$, $COR_4$, $CH_2OH$, $(CH_2)_nOH$, $(CH_2)_nOR_4$;
n=0-4;
m=0-4; and
Z=F, Cl, I or Br.

Examples of useful linkers include, but are not limited to, the following structures:

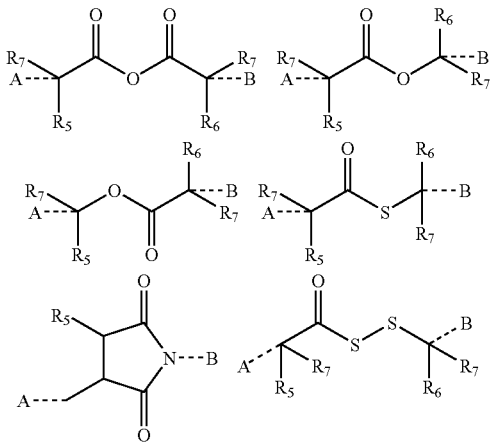

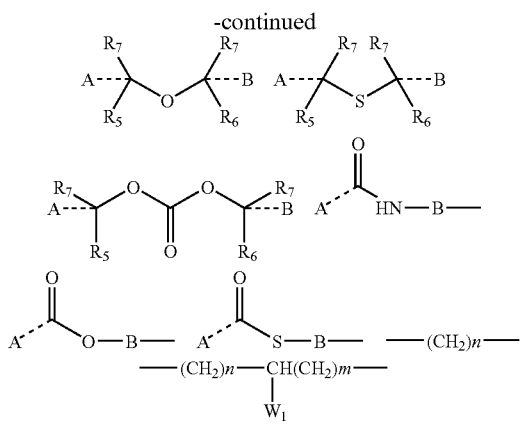

where A and/or B are each individually $=-(CH_2)_n$-D-$(CH_2)_m-$; $D=CH_2$, $(CH_2)_p$, O, S, NH, SO and $SO_2$; $R_5$, $R_6$ and $R_7$ are each individually H, $CH_3$, $(CH_3)_2$, $(CH_2)_nSO_3Q$, alkyl, $(alkyl)_2$, alkenyl, alkynyl, Ar, F, Cl, $OCH_3$; $Q=K^+$, $Na^+$, $Li^+$, $Ca^{2+}$, $NH_4^+$, $RNH_3^+$, or other pharmaceutically acceptable salts; n=0-4; m=0-4, and p=0-3.

Preferred linkers include the following structures: $-(CH_2)_n$ $O(CH_2)_m-$, $-(CH_2)_nOCO(CH_2)_m-$, $-(CH_2)_n COO(CH_2)_m-$, $-(CH_2)_nS(CH_2)_m-$, where n and m=0-4.

Examples of useful Acceptors include, but are not limited to, the following structures:

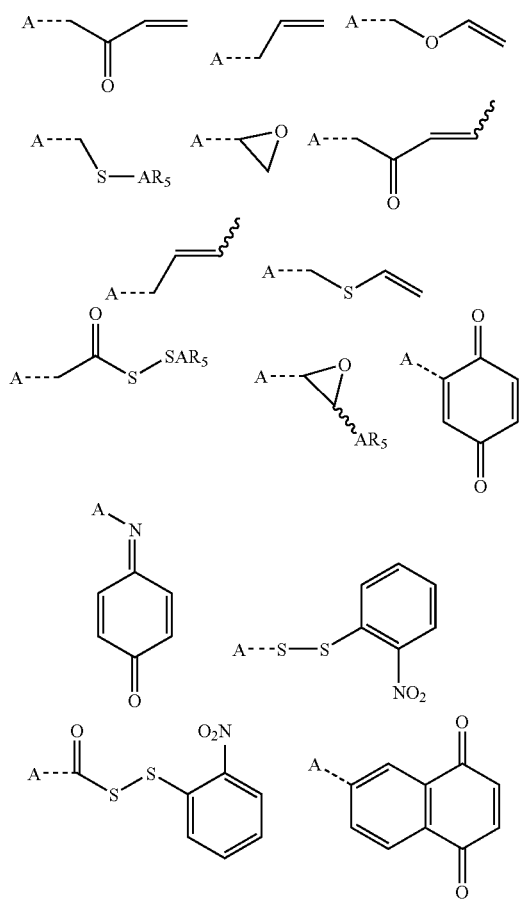

where $A=-(CH_2)_n$-D-$(CH_2)_m-$; $D=CH_2$, $(CH_2)_p$, O, S, NH, SO and $SO_2$; R5 is H, $CH_3$, $(CH_3)_2$, $(CH_2)_nSO_3Q$, alkyl, $(alkyl)_2$, alkenyl, alkynyl, Ar, F, Cl, $OCH_3$.

Preferred acceptors include: $-CH_2CH=CH_2$;

$-CH_2-\underset{\underset{O}{\|}}{N}\underset{\underset{O}{\|}}{\overset{\overset{O}{\|}}{\phantom{N}}}$ and $-CH_2CH\overset{O}{\overset{/\backslash}{C}}H_2$.

In compounds comprising Formula 1, any of the 2-, 3-, 6-, or 7-positions can be α or β. The tropane ring can be unsaturated at any of the 2,3-, 3,4- or 6,7-bonds. In certain embodiments, there can be more than one double bond, e.g., 2,3-, and 6,7- or 3,4- and 6,7-positions. Or, alternatively, the ring can be fully saturated. In certain instances, the compound may be a 6,7-epoxide. The compounds are racemic or have a 1R- or 1S-configuration. In preferred compounds, the compound has Formula 1 and $X=N-R_3$. Preferably, the compound has Formula 1 and $R_2$ is H.

In other embodiments, the compound comprises a ligand having the following Formula 2:

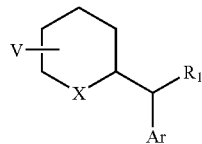

where:

V=H; —Br; —Cl; —I; —F; —OH; —OR$_4$; —CH$_3$; —CF$_3$; —NO$_2$; —NH$_2$; —CN; —NHCOCH$_3$, —C(CH$_3$)$_3$, C(CH$_2$)CH$_3$, (CH$_2$)$_q$CH$_3$, where q=0-6; —COCH$_3$; alkyl; alkenyl; alkynyl; allyl; isopropyl; isobutyl; wherein each substitutent can be at one or more position of the ring;

X, X$_1$, X$_2$, Ar, W, W$_1$, R$_1$, R$_3$, R$_4$, R$_9$, m, n, and Z are as defined above. In these compounds, the 2, or 2'-positions are R or S. The compound may be a 2,2'- or 3,2-unsaturated ene.

In other embodiments, the compound comprises a ligand having the following Formula 3:

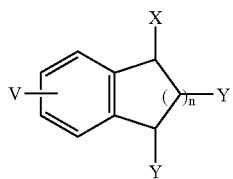

Where:

X, Y (R$_1$ or Ar) are either α or β and where the ring is partially or fully unsaturated;

X=OR$_3$, NHR$_3$, CH$_2$R$_3$, CH$_2$R$_1$, CH$_2$R$_1$, CHR$_1$R$_3$, SR$_3$, SO$_2$R$_3$, SOR$_3$;

Y=R$_1$ and Ar, wherein at least one Y is R$_1$ and at least one Y is Ar;

V, Ar, R$_1$, R$_3$, R$_4$, R$_9$, m, n, and Z are as defined above.

In the compounds of the present invention, Ar is a phenyl substituted with the groups selected from: 3,4-diCl; 3-Cl,4-C(CH$_2$)CH$_3$; 3-Br,4-C(CH$_2$)CH$_3$; 3-I,4-C(CH$_2$)CH$_3$; 4-Cl,3-C(CH$_2$)CH$_3$; 4-Br,3-C(CH$_2$)CH$_3$; 4-I,3-C(CH$_2$)CH$_3$; 3,4-diOH; 3,4-diOAc; 3,4-diOCH$_3$; 3-OH,4-Cl; 3-OH,4-F; 3-Cl, 4-OH; and 3-F,4-OH.

In certain embodiments of the present invention, where the compond comprises a ligand having the structure shown in formula 3, the ligand further has a formula selected from the following:

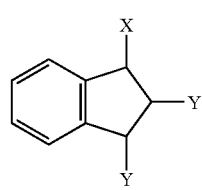

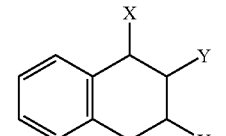

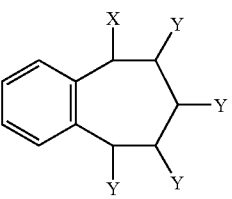

where Y=Ar or R$_1$.

In certain embodiments, having formula 1-4, Ar is phenyl substituted with substituents selected from: one or more —Cl, one or more —F, and a combination of —Cl and —F.

Examples of preferred compounds include: pent-4-enoic acid-(3α-(3,4-dichlorophenyl)-8-oxabicyclo[3.2.1]oct-2β-yl)methyl ester (O-1893); 2β-carbomethoxy-3β-(4-fluorophenyl)-8-[2-(3-oxiranylpropionyloxy)ethyl]-8-azabicyclo[3.2.1]octane (O-1899), 3α-(3,4-dichlorophenyl)-2β-pent-4-enyloxymethyl-8-oxabicyclo[3.2.1]octane (O-2153); 3-Methylbutanoic acid-[3α-(3,4-dichlorophenyl)-8-oxabicyclo[3.2.1]oct-2β-yl]methyl ester (O-2059); Pentanoic acid-[3α-(3,4-dichlorophenyl)-8-oxabicyclo[3.2.1]oct-2β-yl]methyl ester (O-2102); 3-Oxiranyl-propionic acid [3α-(3, 4-dichlorophenyl)-8-oxabicyclo[3.2.1]oct-3β-yl]methyl ester (O-1834); 2β-Carbomethoxy-3β-(4-fluorophenyl)-8-(3-methoxy acetoxypropyl) -8-azabicyclo[3 2.1]octane (O-1071); 2β-Carbomethoxy-3β-(4-fluorophenyl)-8-(2-acetoxyethyl)-8-azabicyclo[3.2.1]octane (O-1103); 2β-Carbomethoxy-3β-(4-fluorophenyl)-8-(2-maleimidoethyl)-8-azabicyclo[3.2.1]octane (O-1233).

Examples of preferred linker-acceptor constructs for use in the present invention include: —(CH$_2$)$_n$CH=CH$_2$; —CH$_2$O(CH$_2$)$_n$CH=CH$_2$; —CH$_2$OCO(CH$_2$)$_n$CH=CH$_2$;

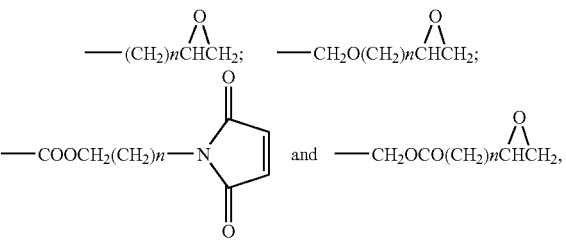

where n=0-4.

Especially preferred constructs include the following:
—CH$_2$OCH$_2$CH$_2$CH=CH$_2$;
—CH$_2$OCOCH$_2$CH$_2$CH=CH$_2$.

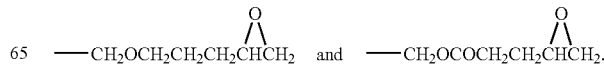

The invention also relates to pharmaceutical compositions comprising a compound comprising a) a ligand for a transporter or receptor and b) a linker-acceptor moiety connected to the ligand, wherein the LAM comprises 1) an acceptor moiety that covalently binds the transporter or receptor and 2) a linker which attaches the ligand to the acceptor moiety in a pharmaceutically acceptable carrier.

In certain embodiments, the compound inhibits binding of cocaine at the monoamine transporter or receptor. In preferred embodiments, the binding of the acceptor moiety to the monoamine transporter allows DA transport.

In other embodiments, the compound inhibits binding of cocaine at a muscarinic cholinergic receptor.

In certain embodiments, the compound comprises a ligand for at least one receptor selected from the group consisting of glutamate transporter, trace amine receptor, opioid receptor, and cannabinoid receptor. In other embodiments the ligand is a ligand for a neurotransmitter receptor.

In certain of the embodiments the compound is further characterized by an $IC_{50}$ of less than 500 nM with respect to [$^3$H]CFT inhibition of DAT. Preferably the $IC_{50}$ is less than 300 nM and most preferably less than 100 nm.

The invention also relates to a method of controlling a patient's response to a substance that acts at a transporter or a receptor, the method comprising administering to the patient an effective amount of a compound comprising a) a ligand for a transporter or receptor and b) a linker-acceptor moiety connected to the ligand, in a pharmaceutically acceptable carrier. Preferred compounds include those having the Formula 1-4. Preferably the compound has the structure shown in Formula 1.

The invention also relates to a method of inhibiting binding of cocaine to the DAT comprising administering an effective amount of a compound as described herein, wherein the transport of dopamine is partially inhibited.

The invention also relates to a method of altering or controlling the binding of serotonin to the SERT comprising administering an effective amount of a compound comprising a) a ligand for the SERT and b) a linker-acceptor moiety connected to the ligand, wherein the LAM comprises 1) an acceptor moiety that covalently binds the transporter or receptor and 2) a linker which attaches the ligand to the acceptor moiety, wherein the transport of serotonin is not completely inhibited.

The invention further relates to a method of treating SERT related disorders, e.g., depression, ADD, ADHD, obsessive compulsive disorder, autism, etc., comprising administering an effective amount of a compound comprising a) a ligand for the SERT and b) a linker-acceptor moiety connected to the ligand, wherein the LAM comprises 1) an acceptor moiety that covalently binds the transporter or receptor and 2) a linker which attaches the ligand to the acceptor moiety, wherein the transport of serotonin is not completely inhibited.

The invention further relates to a method of inhibiting transport of a neurotoxin, e.g., MPP+, through the DAT comprising administering an effective amount of a compound comprising a) a ligand for DAT and b) a linker-acceptor moiety connected to the ligand, comprising 1) an acceptor moiety that covalently binds the transporter or receptor and 2) a linker which attaches the ligand to the acceptor moiety, wherein the transport of dopamine is not inhibited.

The invention also relates to a method of treating Parkinsonism comprising administering an effective amount of a compound comprising a) a ligand for DAT and b) a linker-acceptor moiety connected to the ligand, comprising 1) an acceptor moiety that covalently binds the transporter or receptor and 2) a linker which attaches the ligand to the acceptor moiety, wherein the compound inhibits transport of neurotoxins through the DAT and the transport of dopamine is minimally inhibited.

The details of one or more embodiments of the invention are set forth in the accompanying drawings and the description below. Other features, objects, and advantages of the invention will be apparent from the description and drawings, and from the claims.

DETAILED DESCRIPTION OF THE INVENTION

The term "ligand" as used generally herein refers to a molecule which binds to a receptor or transporter to form a complex.

"Endogenous ligand" as used herein refers to the natural ligand for a receptor or transporter, which is the ligand that is desirable to have transported in a controlled manner. Examples of ligands include, but are not limited to acetylcholine, adenosine, adrenergic, angotensin, bradykinin, calcitonin, Ca++, K+channels, cannabinoid, cholecystokinin, corticotrophin-releasing, cytokine (4 categories), dopamine, endothelin, GABA, galanin, glutamate, glycine, histamine, imidazoline, melatonin, neuropeptide y, neurotensin, opioid, octopamine, orphans, nucleotide, -steroid, non-steroid, protease-activated, P2X; P2Y, serotonin, somatostatin, tachykinin, VIP, vasopressin, oxytocin, nitric oxide.

"Exogenous ligand" as used herein refers to the substance that one wishes to exclude from the transporter or receptor. Examples include cocaine, opiates, MDMA, methamphetamine, amphetamine, neurotoxins, e.g., MPP+, rotenone, nicotine, etc.

"Transporter" as used herein refers to a protein that moves endogenous ligands from the outside of a cell to the interior of the cell or from the cytosol of the cell interior into and out of vesicles and the reverse. Examples of transporters that can be targeted by compounds of the present invention include, but are not limited to, the transporters for dopamine, serotonin, norepinephrine, proline, glutamate, anandamide, glycine, taurine, creatine, GABA, etc.

"Receptor" as used herein generally refers to a protein that binds a ligand and affects the transfer of information into the cell, e.g., triggering an intracellular reaction or affect cell membrane ion conductance. Examples of receptors that can be targeted by compounds of the present invention include, but are not limited to, the receptors for acetylcholine, adenosine, adrenergic, angotensin, bradykinin, calcitonin, Ca++, K+channels, cannabinoid, cholecystokinin, corticotrophin-releasing, cytokine (4 categories), dopamine, endothelin, GABA, galanin, glutamate, glycine, histamine, imidazoline, melatonin, neuropeptide y, neurotensin, opioid, octopamine, orphans, nucleotide, -steroid, non-steroid, protease-activated, P2X; P2Y, serotonin, somatostatin, tachykinin, VIP, vasopressin, oxytocin, nitric oxide.

"Partial agonist" as used herein refers to a compound which possesses affinity for a transporter or receptor, but unlike a full agonist, will elicit only a small degree of the pharmacological response peculiar to the nature of the receptor involved, even if a high proportion of receptors are occupied by the compound.

Figure 4:
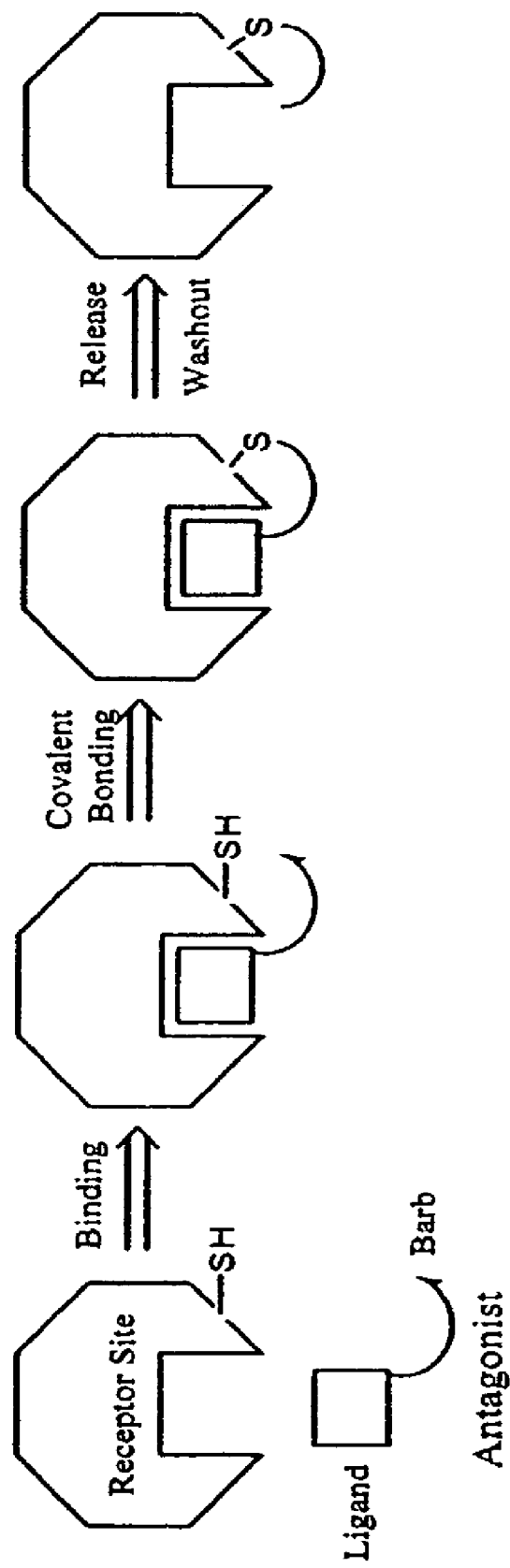
FIG. 4 is a schematic diagram showing the binding of the compounds of the present invention and subsequent release of the ligand.

The ligand portion of the compounds of the present invention is attached, via a cleavable tether or linker, to an acceptor moiety that can bind covalently to an amino acid residue of a protein, e.g. thiol of cysteine, in the vicinity of the binding site of the acceptor moiety. The attack of the receptor site based thiol is then followed by release of the ligand. The portion of the acceptor moiety that remains bound to the binding site is referred to herein as a "barb". As shown in FIG. 4, the barb remains to perturb, or block, the site locally to exogenous ligand. The barb is sufficiently small so as to not block "incoming" endogenous ligand and should also not cause extensive perturbation of the receptor site.

The methods of the present invention are useful in any instance where the acceptor site for the exogenous ligand in question is topologically close enough to the site at which the endogenous ligand binds. Transport mechanisms are especially well-suited for this. However this concept may apply in any receptor or transporter system in which it is desired to block one ligand in preference for another, given that the two ligands bind at slightly different domains on the biological receptor. For purposes of illustration, the dopamine transporter will be described in detail. However, as described herein, the compounds and methods of the present invention can be modified for many types of transporter and receptor systems.

In one embodiment of the present invention, the compounds are partial inhibitors of monoamine reuptake. These compounds target monoamine transporters and/or receptors, particularly neurotransmitter receptors. Such inhibitors of monoamine reuptake can provide medications for the control of general disorders of monoamine systems. The compounds of this disclosure can be used as medications for cocaine abuse, attention deficit disorder, autism, depression, obsessive-compulsive disorder, and generally for neurological and other psychiatric disorders associated with monoamine uptake systems. In an especially preferred embodiment, the compounds deliver an inhibitor that binds irreversibly to the DAT and blocks access by exogenous ligands, e.g., cocaine, but permits dopamine transport. The design of these compounds takes advantage of a cysteinyl sulfhydryl group in the DAT. This group is hypothesized to attack the incoming inhibitor and lead to selective inhibition of the cocaine binding site while sparing dopamine transport. While the invention is not limited to DAT targeting compounds, the invention is described using these compounds.

In the embodiments of the present invention, which are useful for blocking cocaine, the compounds deliver a small non-tropane irreversible DAT inhibitor that blocks DAT access by cocaine but permits DA transport. The compounds of the present invention enable the removal of the bulk of the antagonist from the binding site after an interaction that renders the dopamine transporter unavailable for cocaine, but readily available for dopamine transport. Thus selective and potent compounds bind to the dopamine transporter but, once bound, interact covalently with a proximate amino acid at the cocaine binding site. The bulk of the guiding ligand dissociates, leaving a small residue, or barb, attached.

The compounds and methods of the present invention enable long term modulation of drug effectiveness. The duration of the effect of these partial antagonists is longer than ordinary drug antagonists because turnover of the protein to which the barb is bound is longer than the half-life life of pharmaceutical compositions. This long half-life can induce neuroadaptation which can have secondary therapeutic benefits. Furthermore, the type of modulation of these compounds is different than that of an ordinary drug because the previously used drugs prevents natural endogenous substance from having access to the transporter. Whereas, the compounds of the present invention enable one to prevent transport of exogenous ligand while allowing partial transport of the endogenous ligand.

Ligand:

The ligand serves as a device to guide the molecule specifically and selectively to the transporter or receptor of interest. One of ordinary skill in the art can select the ligand from known ligands in accordance with the knowledge in the art. Examples of ligands for the DAT, e.g., include phenyl tropanes, methylphenidate, indatraline, mazindal, benztropine, etc. Examples of ligands for the SERT include tropanes, sertraline, citalopram, fluoxetine, fluvoxamine, and paroxetine. Useful ligands for other transporters or receptors will be readily apparent to one of ordinary skill in the art based upon the knowledge in the art as well as the teachings contained herein.

In certain preferred embodiments, the ligand is a compound that binds selectively and potently to monoamine transporters. As aforesaid, preferred monoamine transporter targets include DAT, SERT and NET. Ligands for the DAT have been intensively investigated. As a result, the art is aware of a plethora of DAT ligands and those ligands are generally useful in the present invention as a carrier of (targeting agent for) the active barb. Since the DAT ligand may be cleaved after it has served its purpose of locating the transporter, the invention is not limited to any specific DAT ligand. Any of a broad range of ligands may be used and improved upon by techniques known to those skilled in the art.

Examples of preferred ligands for targeting the DAT include, but are not limited to the following:

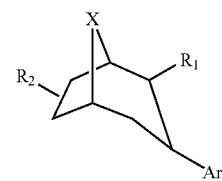

where, the ligand can be 2α and/or 2β, 3α and/or 3β, a 2,3-unsaturated ene or a 3,4-unsaturated ene. Any tropane compound of the above general formula is useful in the present invention so long as it binds to DAT. Examples of particularly useful tropanes are: 2-carbomethoxy-3-(4-fluorophenyl)-N-methyltropane ("WIN 35,428") (Clarke, R. L., et al., *J. Med. Chem.* 1973, 16, 1260-1267) which binds potently ($IC_{50}$=11.0 nM) and with specificity to the DAT (Meltzer, P. C., et al., *J. Med. Chem.* 1993, 36, 855-862); 2-carbomethoxy-3-(3,4-dichlorophenyl)-N-methyltropane ("O-401"; $IC_{50}$=1.09 nM) (Meltzer, P. C., et al., *J. Med. Chem.* 1993, 36, 855-862). Tropane analogs that have a 3α-group are of the boat configuration. Other tropanes having a 3β-oriented group are of the chair configuration. Certain preferred compounds for use in the present invention have the boat configuration.

Other compounds useful in the present invention include the tropanes disclosed in U.S. Pat. Nos. 6,313,105, 6,171,576, 5,948,933, 5,506,359, which are incorporated herein in their entirety. One example includes, e.g., (S)-(+)-2-carbomethoxy-3α-(bis(4-fluorophenyl)methoxy)tropane. Additional examples of preferred tropane compounds are described in U.S. application Ser. Nos. 10/033,621 (filed Dec. 12, 2001), Ser. No. 10/222,530 (filed Aug. 16, 2002) and Meltzer, et al., *J. Med. Chem.* 2001, 44, 2619-2635, which are incorporated herein in their entirety.

Preferred tropanes have the structure shown in Formula 1 where the 2-, 3-, 6-, or 7-positions are α or β;

the compounds are racemic or 1R- or 1S- configured;

X=O, $NR_3$, $NR_9$, $CHR_3$, $CHR_1$, $CH_2$, $CHW_1$, $CW_1W_1$, CO, S, SO, $SO_2$, $NSO_2R_3$, $NSO_2R_1$ or $CX_2W$, with the N, C, O or S atom being a member of the ring;

Ar=Phenyl or 1-naphththyl or 2-naphthyl, unsubstituted or substituted with one or more group selected from: —H; —Br; —Cl; —I; —F; —OH; —$CH_3$; —$CF_3$; —$NO_2$; —$NH_2$; —CN; —$NHCOCH_3$, —$C(CH_3)_3$, —$C(CH_2)$ $CH_3$, $(CH_2)_qCH_3$, where q=0-6; —$COCH_3$; alkyl; alkenyl; alkynyl; allyl; isopropyl; isobutyl; wherein each substitutent can be at the 2, 3 and/or 4 position of the ring;

W or $X_2$=H, OH, $OCH_3$, OAc, $OCOR_4$, $CH_3$, $(CH_2)_nCH_3$, $R_4$;

$W_1$=H, Br, Cl, I, F, OH, $OCH_3$, $CF_3$, $NO_2$, $NH_2$, CN, $NHCOCH_3$, $N(CH_3)_2$, $(CH_2)_nCH_3$, $COCH_3$, or $C(CH_3)_3$;

$X_1$=$NR_3$, $CH_2$, $CHR_4$, $CR_3R_4$, CO, O, S; SO, $SO_2$, $NSO_2R_1$, or $NSO_2R_3$;

$R_1$=H, $COOCH_3$, $COOR_4$, $COR_4$, $CH_2OH$, $(CH_2)_nOH$, $(CH_2)_nOR_4$, $CR_3$=$NOR_3$, CH=$NR_3$;

$R_2$=H, OH, $OCOR_4$, $OCOR_5$, where $R_5$ is not F, Cl;

$R_3$=H, $CH_3$, $CH_2Ar$, $(CH_2)_nAr$, Ar, lower alkyl, lower alkenyl or lower alkynyl; $CH_2CH$=CHZ, $(CH_2)_nOH$, $(CH_2)_nOR_4$, CH=CHZ; $CH_2$J-Maleimide, $CH_2$JN-Maleimide where J=$CH_2$ or O; $(CH_2)_nOCOCH_3$; $(CH_2)_nOCOCH_2OCH_3$; $(CH_2)_n$-morpholine; $(CH_2)_n$-piperidine; $(CH_2)_n$-piperazine;

$R_4$=$CH_3$, $CH_2CH_3$, alkyl, alkenyl, alkynyl, allyl, isopropyl, isobutyl;

$R_9$=H, $COOCH_3$, $COOR_4$, $COR_4$, $CH_2OH$, $(CH_2)_nOH$, $(CH_2)_nOR_4$;

n=0-4;

m=0-4; and

Z=F, Cl, I or Br.

Other compounds useful as ligands that bind DAT include a ligand having the following Formula 2:

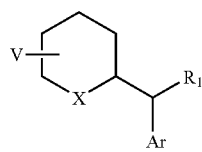

2 where V, X, $X_1$, $X_2$, Ar, W, $W_1$, $R_1$, $R_3$, $R_4$, $R_9$, m, n, and Z are as defined above. In these compounds, the 2, or 2'-positions are R or S. The compound may be a 2,2'- or 3,2-unsaturated ene.

In other embodiments, the compound for binding to DAT comprises a ligand having the following Formula 3:

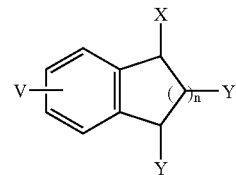

3

Where:

X, Y ($R_1$ or Ar) are either α or β and where the ring is partially or fully unsaturated;

X=$OR_3$, $NHR_3$, $CH_2R_3$, $CH_2R_1$, $CH_2R_1$, $CHR_1R_3$, $SR_3$, $SO_2R_3$, $SOR_3$;

Y, V, Ar, $R_1$, $R_3$, $R_4$, $R_9$, m, n, and Z are as defined above.

In certain embodiments, the ligand has a formula selected from the following:

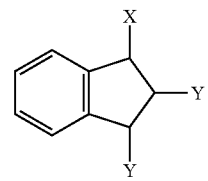

4

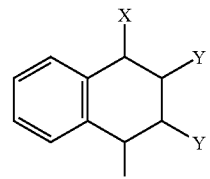

5

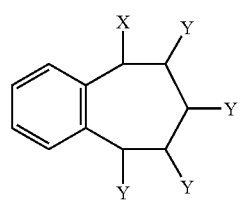

6 where Y=Ar or $R_1$.

Compounds having the structure of Formula 5, which are related to sertraline are especially useful for targeting SERT.

The ligand can be selected on the basis of its selectivity of binding to one type of monoamine transporter as compared with another type. For example, certain compounds of the invention preferentially bind to DAT rather than SERT, or vice versa. That is, certain preferred ligands used in the present invention have a high selectivity for the DAT versus the SERT. For example, ligands may have a SERT/DAT ratio based on $IC_{50}$ of greater than about 10, preferably greater than about 30 and more preferably 100 or more. Other ligands have an $IC_{50}$ at the DAT of less than about 500 nM, preferably less than 200 nM, more preferably less than about 100, and most preferably less than about 60. Using the combination of selectivity (SERT/DAT ratio) and potency (IC50) information for these compounds, one of ordinary skill in the art can readily select the appropriate compound for the desired application.

The 8-oxabicyclo[3.2.1]octane family has provided an array of DAT binding agents. For example, 2β-carbomethoxy-3α-(3',4'-dichlorophenyl)-8-oxabicyclo[3.2.1]octane, a potent (DAT $IC_{50}$=2.34 nM) and reasonably selective (SERT $IC_{50}$=31 nM) compound, provides an example of a useful ligand.

In schizophrenia, partial agonists are explored to reduce the effect of dopamine by targeting dopamine receptors. The basic mechanism of conventional antipsychotic drugs is to block the D2 receptors on the dopamine-responding cells. However, the complete blockade at the dopamine receptors also causes side effects such as muscle stiffness and unintended movements (e.g., tardive dyskensia), as well the inability to still restless legs. In fact these drugs cause the patient to feel overtranquilized. The brain adapts to these drugs, and can lead to irreversible, undesirable, uncontrollable oral-facial or truncal movements. The methods of the present invention can be used to create a drug that treats schizophrenia with longer duration but allows partial access of dopamine on the receptor that is necessary for normal cell function and attenuation of these side effects. Using the methods of this invention, it is possible to target the dopamine receptor and leave a barb behind to allow dopamine to get through. In such a case, it would create a partially functional receptor, which may have antipsychotic effect.

In certain embodiments of the present invention, the ligands target the serotonin transporter (SERT). Ligands that are useful are known in the art and include those described in U.S. application Ser. No. 10/085,482 (filed Feb. 28, 2002) (incorporated herein in its entirety), which describes tropane compounds lacking an amine group and show surprisingly effective results in treating certain neuropsychiatric disorders related to serotonin transport. Preferred compounds have a SERT/DAT selectivity ratio of at least about 3. Other embodiments have a SERT/DAT selectivity ratio of at least about 8 and other preferably at least about 50.

Preferred ligands for binding the SERT have a potency (Ki), or IC50, at the SERT of less than about 500 nM, preferably less than about 100 nM. In certain preferred embodiments the compounds have a Ki at the SERT less than about 50 nM, preferably less than about 25 nM and more preferably less than about 15 nM. Especially preferred compounds have a SERT/DAT selectivity ratio of at least about 3 and an IC50 at the SERT of less than about 500 nM.

The compounds and methods of the present invention can also be used where it is desirable to have partial blockage of a transporter or receptor, e.g., where it is desirable to decrease the accumulation of an endogenous ligand in extracellular fluid. For example, as discussed previously, SSRIs are used to treat major depression, dysthymia, panic disorder, obsessive-compulsive disorder, eating disorders, and premenstrual dysphoric disorder, which are believed to be caused by excess serotonin in the brain. SSRIs are effective by reducing the uptake of serotonin through serotonin transporters (SERT) into brain cells. However, presently used drugs can be so effective at decreasing serotonin transport that side effects, due to the blockade of sertonin transport in the brain can occur. Side effect may also result from drug effects on other brain proteins. Side effects include gastrointestinal disturbances, headache, sedation, insomnia, activation, weight gain, impaired memory, excessive perspiration, paresthesia, and sexual dysfunction. Thus, the compounds of the present invention can be used to partially inhibit serotonin transport, i.e., to allow a "normal" amount of serotonin to be transported into brain cells. In such a case, ligand that are known to target the SERT can be used as the ligand. For example, presently known SSRI's can be used as the ligand, including citalopram (Cipramil), fluoxetine (Prozac), fluvoxamine (Faverin), paroxetine (Seroxat), and sertraline (Lustral).

Similar methods can be used with TCAs to minimize the side effects associated with those drugs. As aforesaid, TCAs work by raising the levels of serotonin and norepinephrine in the brain by slowing the rate of transport, or reabsorption, by nerve cells. TCAs tend to affect other brain proteins as well, and have more unpleasant side effects than SSRIs and include drowsiness, anxiety, restlessness, dry mouth, constipation, urinary retention, difficulty urinating, cognitive and memory difficulties, weight gain, increased sweating, dizziness, decrease in sexual ability and desire, muscle twitches, fatigue, weakness, nausea, increased heart beats, irregular heart rhythms (very rare). The compounds of the present invention can be used to reduce the side effects of tricyclic antidepressants by allowing partial transport of serotonin that is necessary for normal cell function. In these cases, the TCA could be used as the ligand. Examples of TCAs include imipramine (Tofranil), amitriptyline (Elavil) and nortriptyline (Pamelor).

The norepinephrine transporter (NET), another monoamine transporter, has a major role in terminating the neurochemical signal established by the neurotransmitter norepinephrine (NE) in the synapse. The NET is also the initial site of action for therapeutic antidepressants, and drugs such as cocaine and amphetamines. Drugs of abuse such as amphetamine and cocaine, and antidepressants (e.g. desipramine, imipramine, venlafaxine, mirtazapine, reboxetine, bupropion), block the transport of NE, and result in an elevation of the synaptic concentrations of NE and potentiation of the activation of postsynaptic receptors (Trendelenburg, U. (1991), *Trends Pharmacol Sci* 12, 334-337; Amara, S. G. and Sonders, M. S. (1998) *Drug Alcohol Depend* 51, 87-96). See Tellioglu, T. et al., (2001) *Exp. Rev. Mol. Med.* 19 November. Compounds of the present invention that target NET, and influence NE transport, may also have a therapeutic benefit. For example, Atomoxetine has been approved for treatment of ADHD and may prove useful in the methods of the present invention.

The methods of the present invention can be used to target receptors other than monoamine receptors and transporters. For example, compounds can be developed using the teachings disclosed herein to target the trace amine receptor. The trace amines are molecules that are found in human bodies in low amounts. The trace amines are structurally related to the neurotransmitters dopamine, adrenaline and serotonin and have long been suspected of having effects on body temperature, blood pressure, mood, depression and sexual dysfunction. Depressed patients have less than normal concentrations of beta-phenylethylamine (beta-PEA) and tyramine (both trace amines) in their urine. Children with Attention Deficit Hyperactivity Disorder have higher than normal concentrations of beta-PEA. Prozac and MAOIs alter the concentrations of trace amines in the brain. In addition, these TARs provide a target for mood-altering drugs, such as amphetamines and ecstasy. Thus, the teachings of the present invention can be used to develop compounds that can be used to modulate binding of ligands to TARs. Such compounds that target the TARs can use any ligand that binds a TAR receptor. Such ligands are known in the art and include Tyramine, Tryptamine and beta-Phenythylamine (beta-PEA).

Other embodiments of the present invention target the opioid receptor. There are three well-defined or "classical" types of opioid receptor μ,Δ and κ. The compounds that bind these receptors include opiates and opioids. An opiate is defined as a compound containing the fundamental morphine or thebaine structure possessing some affinity to any, or all, of the opioid receptor subtypes. Examples are heroin, buprenorphine and naltrexone. An opioid is any compound, peptide or otherwise, which, while not containing the fundamental morphine or thebaine structure, possesses some affinity for any, or all, of the opioid receptor subtypes. Common opioids are endorphin, fentanyl and methadone. The compounds and methods of the present invention can be used to block the effect of these opiates and opioids on the opioid receptor. Any ligand that would target an opioid receptor can be used as a ligand. Such compounds are useful for drug abuse treatment and prevention. For example, such compounds can be used for treatment of heroine addition by acting as a partial agonist, which is desirable for reducing addiction.

Other embodiments of the present invention target the cannabinoid receptor. Cannabis (marijuana, hashish, ganja, dagga, etc.) is the most widely used illicit substance in the Western world. There are about 60 cannabinoids, the best-known of which are delta-9-tetrahydrocannabinol (THC), cannabidiol (CBD) and cannabinol (CBN). The psychoactive constituents of cannabis produce their pharmacological effects by working at specific receptor sites in the brain. See "On the Cannabinoid Receptor: A Study in Molecular Psychiatry," Roy H. Hart, M.D., Psychiatric Times, July 1997, Vol. XIV, Issue 7. In these embodiments, the ligand binds to the cannabis receptor. A partial agonist may have therapeutic benefit in treating cannabis addiction.

Other embodiments of the present invention can be used to treat nicotine addiction and help promote smoking cessation. Examples of useful ligands are known in the art (e.g., WO 01/89524, incorporated herein in its entirety).

In addition, compounds that modulate GABA receptor activity would be useful anti-anxiety drugs.

Linker-Acceptor Moiety

The Linker-acceptor moiety connects the "barb" to the ligand. It comprises a linker or tether group connected to an acceptor moiety. The linker, i.e., tether, links the acceptor moiety to the ligand. This can be placed at any position on the ligand that would enable the cleavage of the cleavable bond. For example, the C2-position of the 8-oxabicyclo[3.2.1]octanes is an optimal position for the linker. Other positions include the bridge substituent, e.g., "X", or $R_2$, or AR in Formula 1. Preferably the linker is attached at X or $R_1$. In compounds having the ligand shown in Formula 2, the linker can be attached at any of V, X, Ar or $R_1$. In compounds that have the ligand shown in Formulae 3-6, the linker can be attached at any of V, X or any of the Y positions. The linker is attached to at least one position on the ligand and preferably, no more than at two positions on the ligand.

Optionally, the compound is cleaved over a relatively short time under physiological conditions, either spontaneously or by enzymatic action. Cleavage time ideally will range from immediate to 24 hours, although the invention will be useful if some cleavage (even most of the cleavage) occurs after that range. Those in the art will understand that many functional groups can be stable components of a medication, with controlled cleavage under physiological conditions. The cleavable bonds may include, for example, an ester, an ether, a thioester, a thioether or an amide bond that can be hydrolyzed spontaneously or enzymatically under physiological conditions. The cleavable bond may be part of a chain, e.g. one that is saturated or unsaturated. Specific linkers that are useful will be apparent from the following description of the preferred compounds.

Any linker that is known in the art can be used provided that it can connect the acceptor moiety to the ligand and is cleavable. Examples of linkers include, but are not limited to:

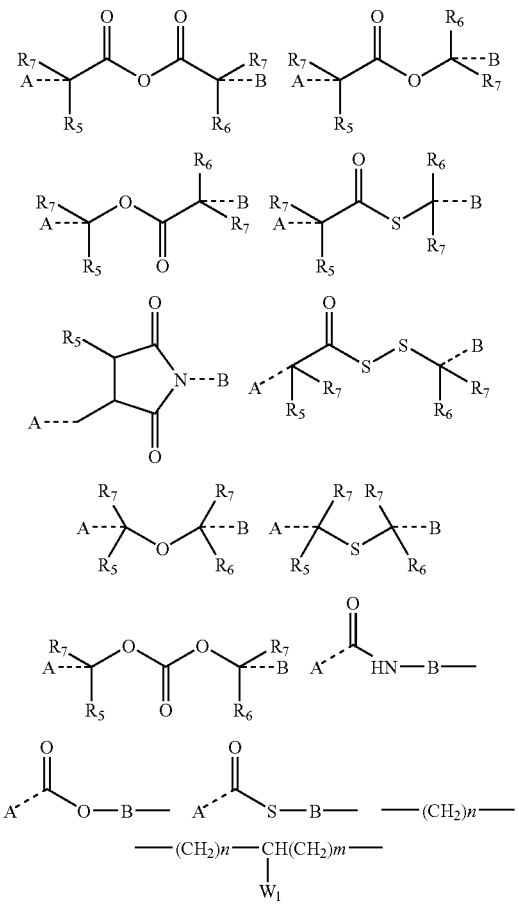

where A and B are each individually=—$(CH_2)_n$-D-$(CH_2)_m$—, D=$CH_2$, $(CH_2)_p$, O, S, NH, SO and $SO_2$.

Preferred linkers include —$(CH_2)_n O(CH_2)_m$—, —$(CH_2)_n OCO(CH_2)_m$—, —$(CH_2)_n COO(CH_2)_m$—, —$(CH_2)_n S(CH_2)_m$—, where n and m=0-4.

The Acceptor Moiety can be a nucleophile acceptor such as an epoxide or double bond, capable of tight binding to the biological target. Alternatively, the Acceptor Moiety may be an electrophile acceptor or a radical acceptor. A portion of the Acceptor Moiety remains bound to the target subsequent to the cleavage of the linker to produce the barb. Examples of Acceptor Moieties include, but are not limited to the following structures:

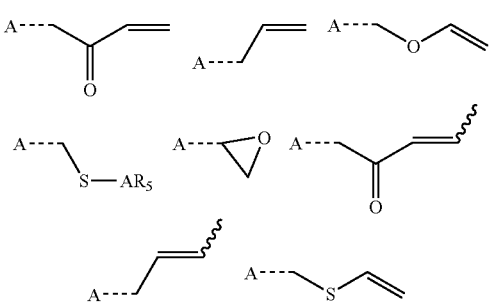

-continued

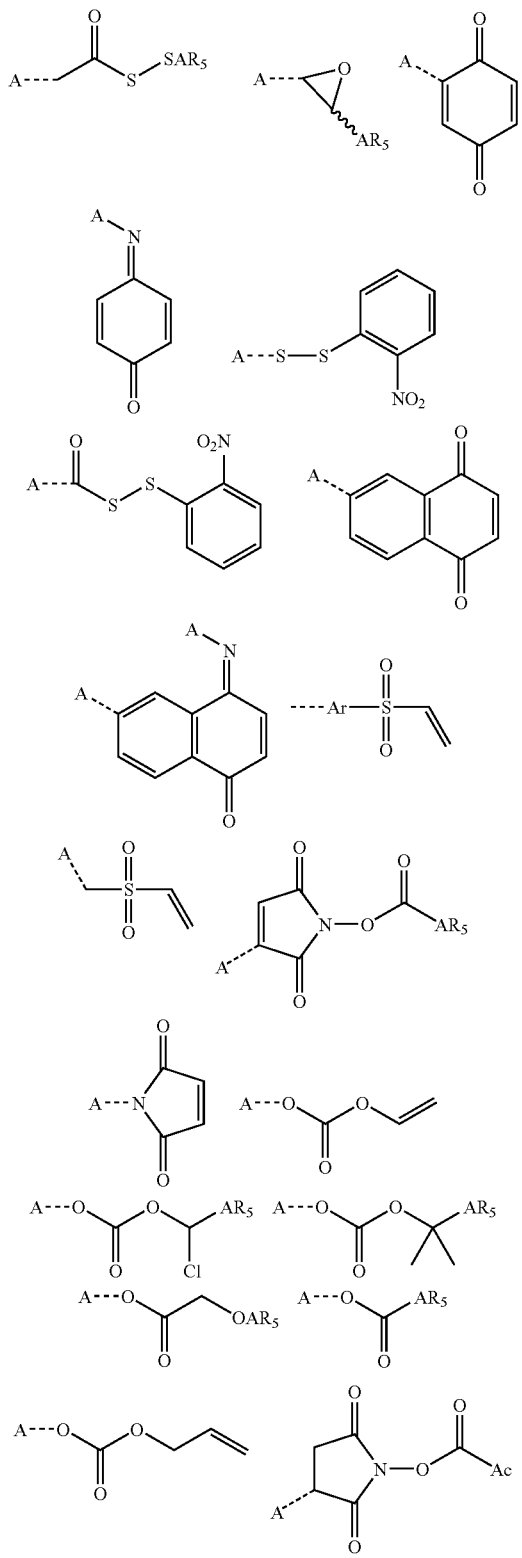

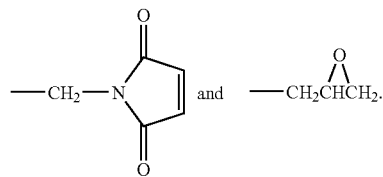

The selection of appropriate barb functionality depends on the relative kinetics required in order for the delivery, binding, reaction, release, and washout to occur in sequential order. Specifically, the rate of interaction of the barb with a thiol is preferably slower than the rate of delivery of the ligand to the site of action itself as well as binding to that acceptor site. However, once within the binding site, the attack upon the incoming ligand should be efficient in order to avoid washout of the ligand prior to covalent binding. The subsequent cleavage of the ligand should be slower than the interaction with the cysteine in order to avoid cleavage of the molecule prior to delivery, binding, and covalent attachment at the active site. However, this cleavage, once within the acceptor site, should be complete, with release of the ligand moiety. The washout rate of the released ligand moiety will then determine the onset time of the antagonist as well as its efficacy. The duration of action of the successful antagonist will then be determined by the relative turnover rate of the transporter or receptor itself. These considerations will help guide one of ordinary skill in the art to select a suitable acceptor moiety and ligand.

Specific barbs that are useful will be apparent from the description of the preferred compounds included herein.

Examples of useful linker-acceptor complexes include the following:

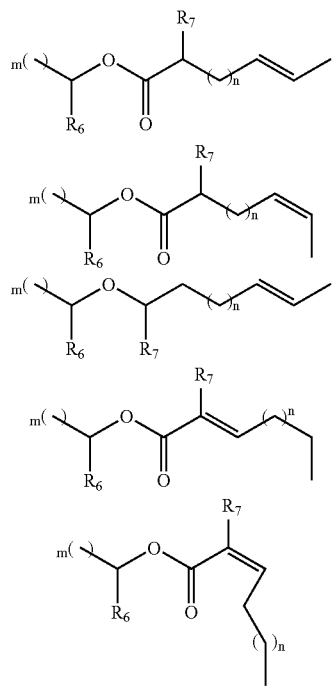

where $R_5$ is H, $CH_3$, $(CH_3)_2$, $(CH_2)_nSO_3Q$, alkyl, $(alkyl)_2$, alkenyl, alkynyl, Ar, F, Cl, $OCH_3$. Preferably, the Acceptor Moieties comprise, but are not limited to, an epoxide or a double bond. Preferred acceptors include: $—CH_2CH=CH_2$;

-continued
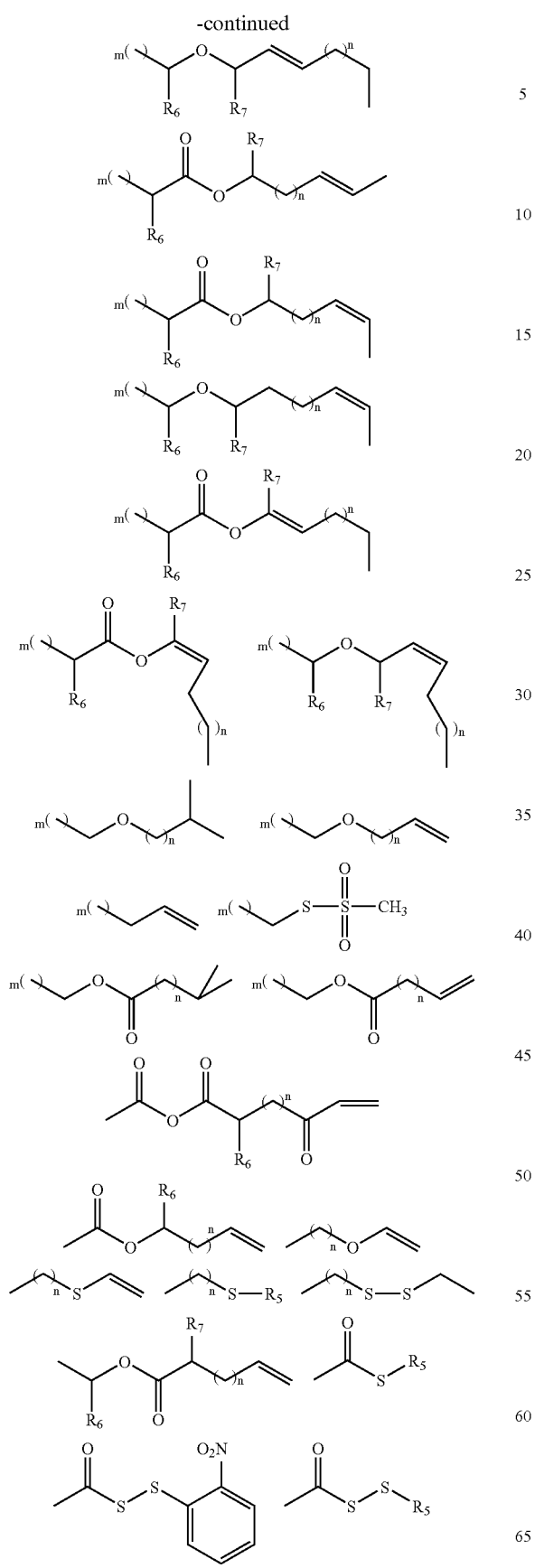
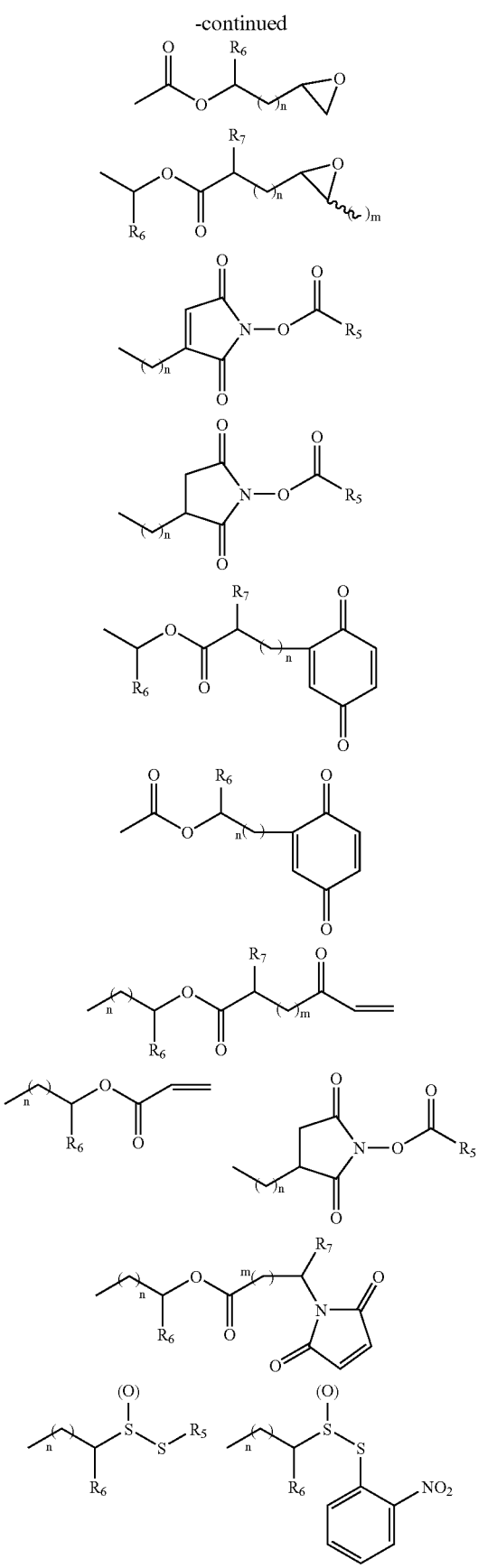

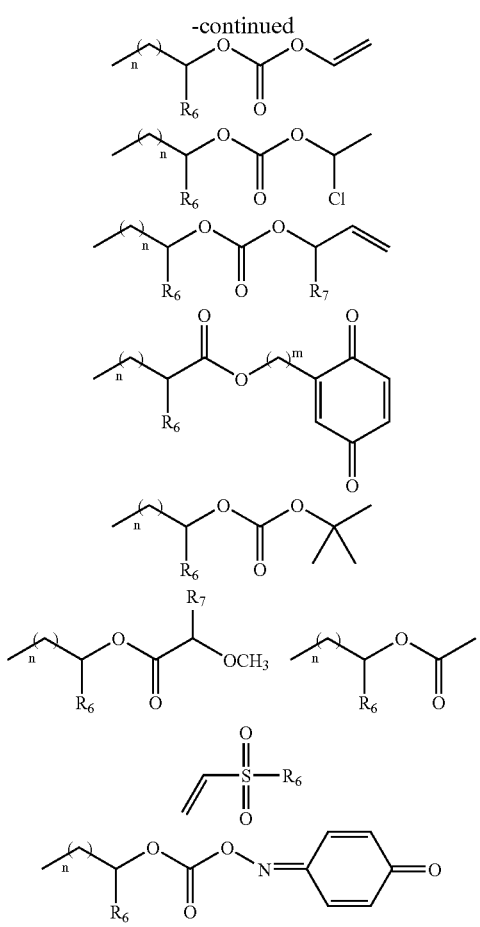

where $R_5$, $R_6$, and $R_7$ are each selected from H, $CH_3$, $(CH_3)_2$, alkyl, $(alkyl)_2$, alkenyl, alkynyl, Ar, F, Cl, $OCH_3$; n=0-4; and m=0-4.

Preferred linker-acceptor constructs include: $-(CH_2)_n CH=CH_2$; $-CH_2O(CH_2)CH=CH_2$; $-CH_2OCO(CH_2)_n CH=CH_2$;

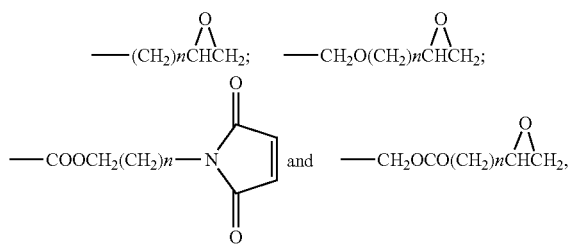

where n=0-4.

Especially preferred constructs include the following:
$-CH_2OCH_2CH_2CH=CH_2$;
$-CH_2OCOCH_2CH_2CH=CH_2$;

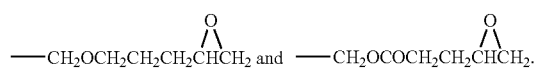

Preferred Compounds

Preferred compounds of the present invention comprise a tropane ligand. The substituents at the 2 position of the tropane ring can be α- or β. Preferred compounds have the substitutents at the 3-position in the α configuration to form the boat conformation. Although $R_1$ is illustrated in the 2-position, it should be recognized that substitution at the 4-position is also included and the position is dependent on the numbering of the tropane ring. The compounds of the present invention can be racemic, pure R-enantiomers, or pure S-enantiomers. Thus, the structural formulas illustrated herein are intended to represent each enantiomer and diastereomer of the illustrated compound.

Preferred embodiments have the following structure:

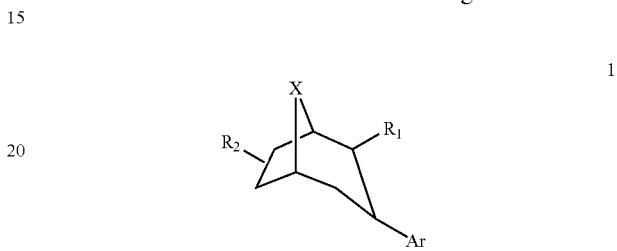

Where:
the 2-, 3-, 6-, or 7-positions are α or β;
the compounds are racemic or 1R- or 1S-configured;
$X=O$, $NR_3$, $NR_9$, $CHR_3$, $CHR_1$, $CH_2$, $CHW_1$, $CW_1W_1$, CO, S, SO, $SO_2$, $NSO_2R_3$, $NSO_2R_1$ or $CX_2W$, with the N, C, O or S atom being a member of the ring;
Ar=Phenyl or 1-naphththyl or 2-naphthyl, unsubstituted or substituted with one or more group selected from: —H; —Br; —Cl; —I; —F; —OH; —$OR_4$; —$CH_3$; —$CF_3$; —$NO_2$; —$NH_2$; —CN; —$NHCOCH_3$, —$C(CH_3)_3$, —$C(CH_2)CH_3$, $(CH_2)_q CH_3$, where q=0-6; —$COCH_3$; alkyl; alkenyl; alkynyl; allyl; isopropyl; isobutyl; wherein each substitutent can be at the 2, 3 and/or 4 position of the ring;
W or $X_2$=H, OH, $OCH_3$, OAc, $OCOR_4$, $CH_3$, $(CH_2)_n CH_3$, $R_4$;
$W_1$=H, Br, Cl, I, F, OH, $OCH_3$, $CF_3$, $NO_2$, $NH_2$, CN, $NHCOCH_3$, $N(CH_3)_2$, $(CH_2)_n CH_3$, $COCH_3$, or $C(CH_3)_3$;
$X_1=NR_3$, $CH_2$, $CHR_4$, $CR_3R_4$, CO, O, S; SO, $SO_2$, $NSO_2R_1$, or $NSO_2R_3$;
$R_1$=H, $COOCH_3$, $COOR_4$, $COR_4$, $CH_2OH$, $(CH_2)_n OH$, $(CH_2)_n OR_4$, $CR_3=NOR_3$, $CH=NR_3R_8$;
$R_2$=H, OH, $OCOR_4$, $R_8$, $OCOR_5$, where $R_5$ is not F, Cl;
$R_3$=H, $CH_3$, $CH_2Ar$, $(CH_2)_n Ar$, $R_8$, Ar, lower alkyl, lower alkenyl or lower alkynyl; $CH_2CH=CHZ$, $(CH_2)_n OH$, $(CH_2)_n OR_4$, $CH=CHZ$; $CH_2$J-Maleimide, $CH_2$JN-Maleimide where $J=CH_2$ or O; $(CH_2)_n OCOCH_3$; $(CH_2)_n OCOCH_2 OCH_3$; $(CH_2)_n$-morpholine; $(CH_2)_n$-piperidine; $(CH_2)_n$-piperazine;
$R_4=CH_3$, $CH_2CH_3$, alkyl, alkenyl, alkynyl, allyl, isopropyl, isobutyl, $R_8$;
$R_9$=H, $COOCH_3$, $COOR_4$, $COR_4$, $CH_2OH$, $(CH_2)_n OH$, $(CH_2)_n OR_4$, $R_8$;
$R_8=(CH_2)_n OCH_2CH=CH_2$; $COD(CH_2)_n CH=CH_2$; $(CH_2)_n D(CH_2)_m CH=CH_2$;
$(CH_2)_n SCH_2CH=CH_2$; $(CH_2)_n OCH_2(CH_2)_n CH=CH_2$; $(CH_2)_n CH=CH_2$;
$(CH_2)_n OCO(CH_2)_m CH=CH_2$; $(CH_2)_n OCO(CH_2)_m CH—(O:epoxide)—CH_2$;
$(CH_2)_n OCO$ $(CH_2)_m CH_3$; $(CH_2)_n OCO(CH_2)_m OCH_3$; $(CH_2)_n OCOCH(CH_3)_3$;

$(CH_2)_nOCO(CH_2)_mCH(CH_3)_2$; $(CH_2)_nOCO(CH_2)_mCH_3$; $(CH_2)_nOCOCH_2CH(R_2)_2$;
$(CH_2)_nOCOCHR_4CH(R_2)_2$; $(CH_2)_nOCOCHCHR_2$; $(CH_2)_nOCHCH(R_2)_2$; $(CH_2)_n$ J-Maleimide, $(CH_2)_n$JN-Maleimide; $COO(CH_2)_m$-Maleimide; $(CH_2)_nOCOCH_3$; $(CH_2)_nOCOCH_2OCH_3$;

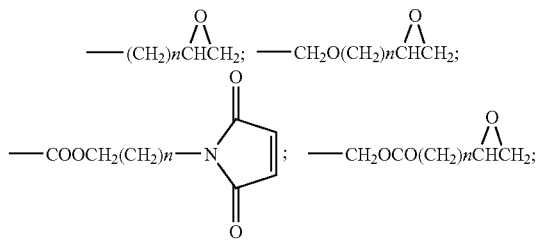

or a linker acceptor construct comprising Linker and Acceptor as defined herein;
$D=CH_2$, $(CH_2)_p$, O, S, NH, SO and $SO_2$;
wherein $R_8$ is at one or two of $R_1$, $R_2$, $R_3$, $R_4$ or Ar;
n=0-4; m=0-4; p=0-3; and
Z=F, Cl, I or Br.

The substitutions on the AR group can be at any position, i.e., at the 2, 3 and/or 4 position, that is chemically possible based upon the selected substituent and AR group. The aryl ring can be substituted with chloride, fluoride or iodide. Ar may be a mono- or di-halogen substituted phenyl. In certain embodiments, e.g., the substituent has the following positions: 4-F, 4-Cl, 4-I, 4-OH, 2-F, 2-Cl, 2-I, 2-OH, 3-F, 3-Cl, 3-I, 3-OH. Preferably the substituent is a halogen. In certain embodiments, the amino group is a mono- or di-alkyl substituted group having from 1-8 carbon atoms.

Alkyl designates aliphatic saturated branched or straight chain hydrocarbon monovalent substituents, having up to 20 carbons, including all lengths from 1 to 20. Lower alkyl designates aliphatic saturated branched or straight chain hydrocarbon monovalent substituents having 1 to about 8 carbons atoms, such as methyl, ethyl, isopropyl, n-propyl, n-butyl, $(CH_2)_nCH_3$, and $C(CH_3)_3$. Alkyl refers to both cyclic and noncyclic groups, although cyclic groups will comprise at least three carbon ring atoms.

Alkenyl and alkynyl groups of compounds of the invention have up to 20 carbons and have one or more unsaturated linkages. Also, the terms alkenyl and alkynyl as used herein refer to both cyclic and noncyclic groups.

Alkoxy groups of compounds of the invention have a length of up to 20 carbons and have one or more oxygen linkages. Lower alkoxy designates lower alkoxy substituents such as methoxy, ethoxy, or isopropoxy moieties. The lower alkyl and lower alkoxy substituents are from one to about 8 carbons in length, and in one embodiment are from one to about four carbons in length. Lower alkenyl means aliphatic unsaturated branched or straight chain vinyl hydrocarbon substituents such as allyl, etc. Lower alkynyl includes alkynyl substituents such as propyne or butyne; either of these substituent types may contain from 2 to about 8 carbon atoms, and in one embodiment from 2 to 4 carbon atoms.

Substituted alkyl, substituted alkoxy, substituted alkenyl and substituted alkynyl are intended to include corresponding alkyl, alkoxy, alkenyl or alkynyl groups substituted with halide, hydroxy, carboxylic acid, or carboxamide groups such as —$CH_2OH$, —$CH_2CH_2COOH$, —$CH_2CONH_2$, —$OCH_2CH_2OH$, —$OCH_2COOH$, and —$OCH_2CH_2CONH_2$.

Synthesis

Figure 1:
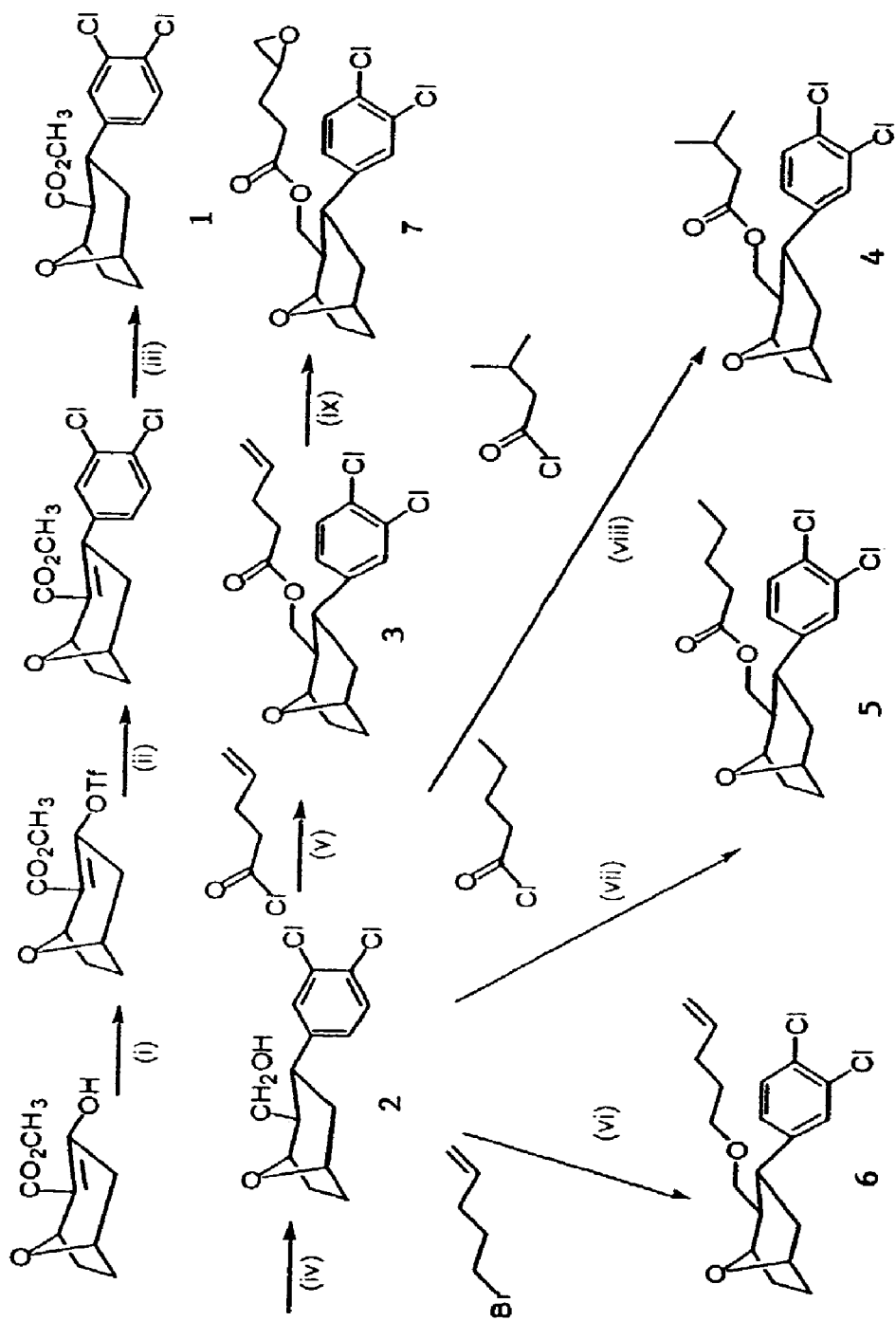
FIG. 1 is a diagram showing synthetic scheme 1, described below, for C2-substituted compounds in the 8-oxa series.
Figure 2:
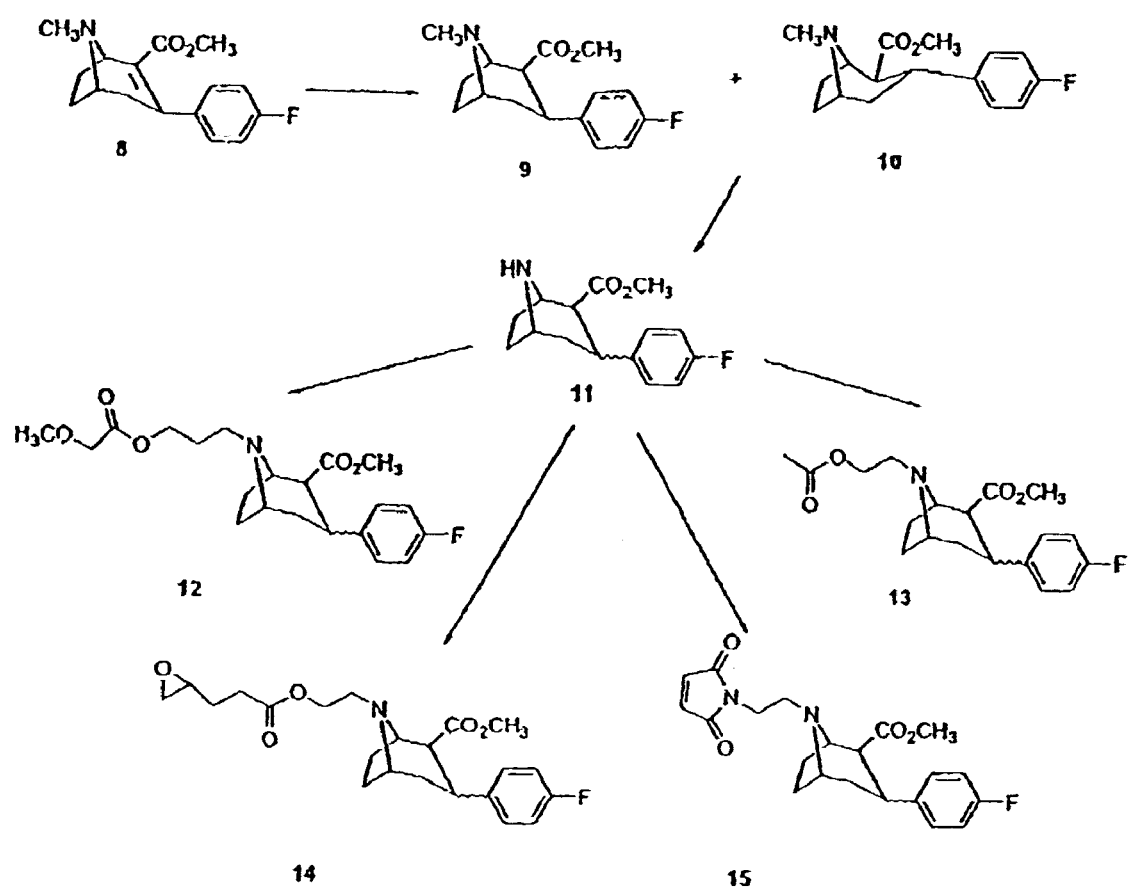
FIG. 2 is a diagram showing synthetic scheme 2, described below, for C2-substituted compounds in the 8-aza series or N-substituted compounds in the 3-aza series.
Figure 3A:
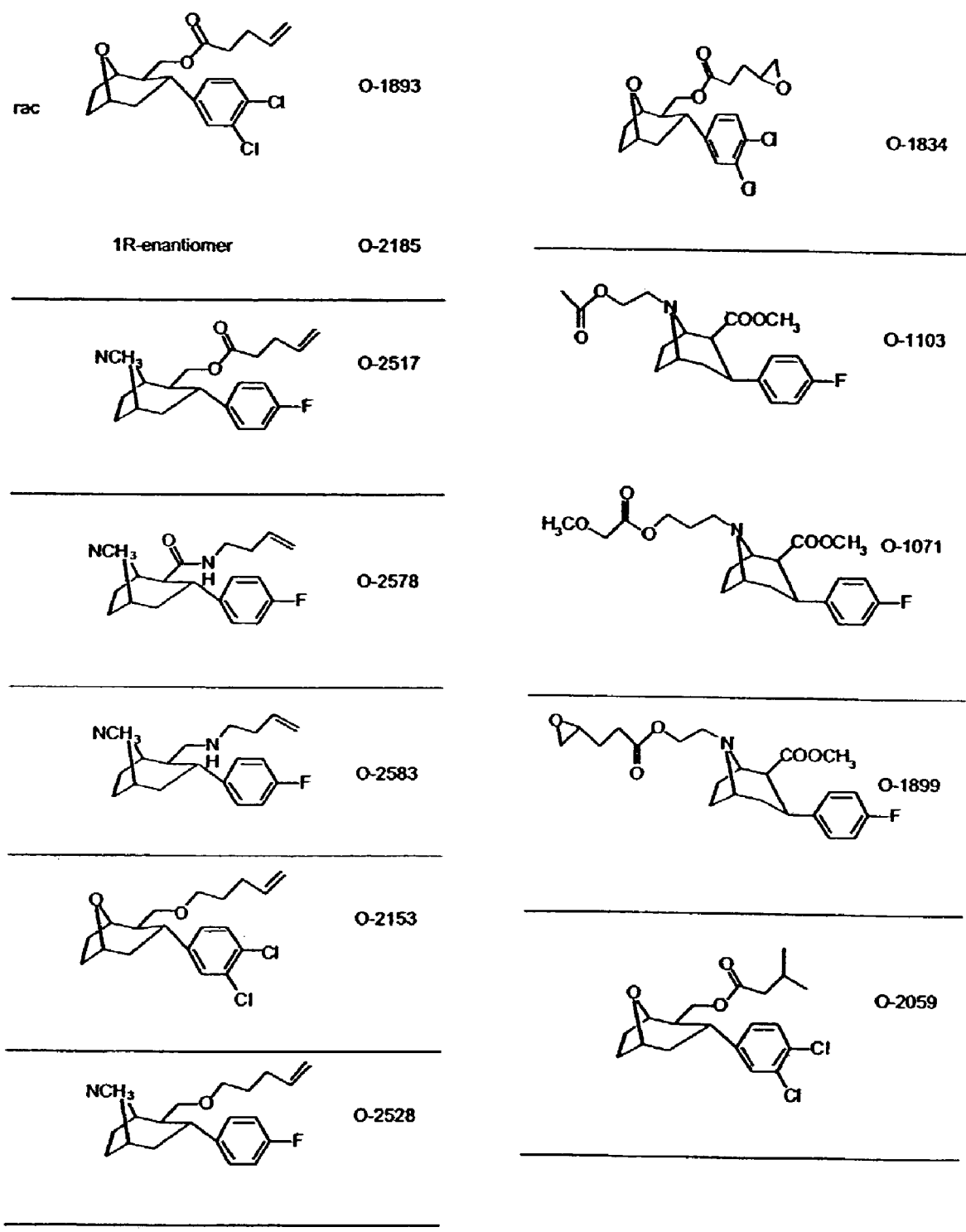
FIGS. 3 (A-C) show the structure of some of the compounds discussed below.
Figure 3B:
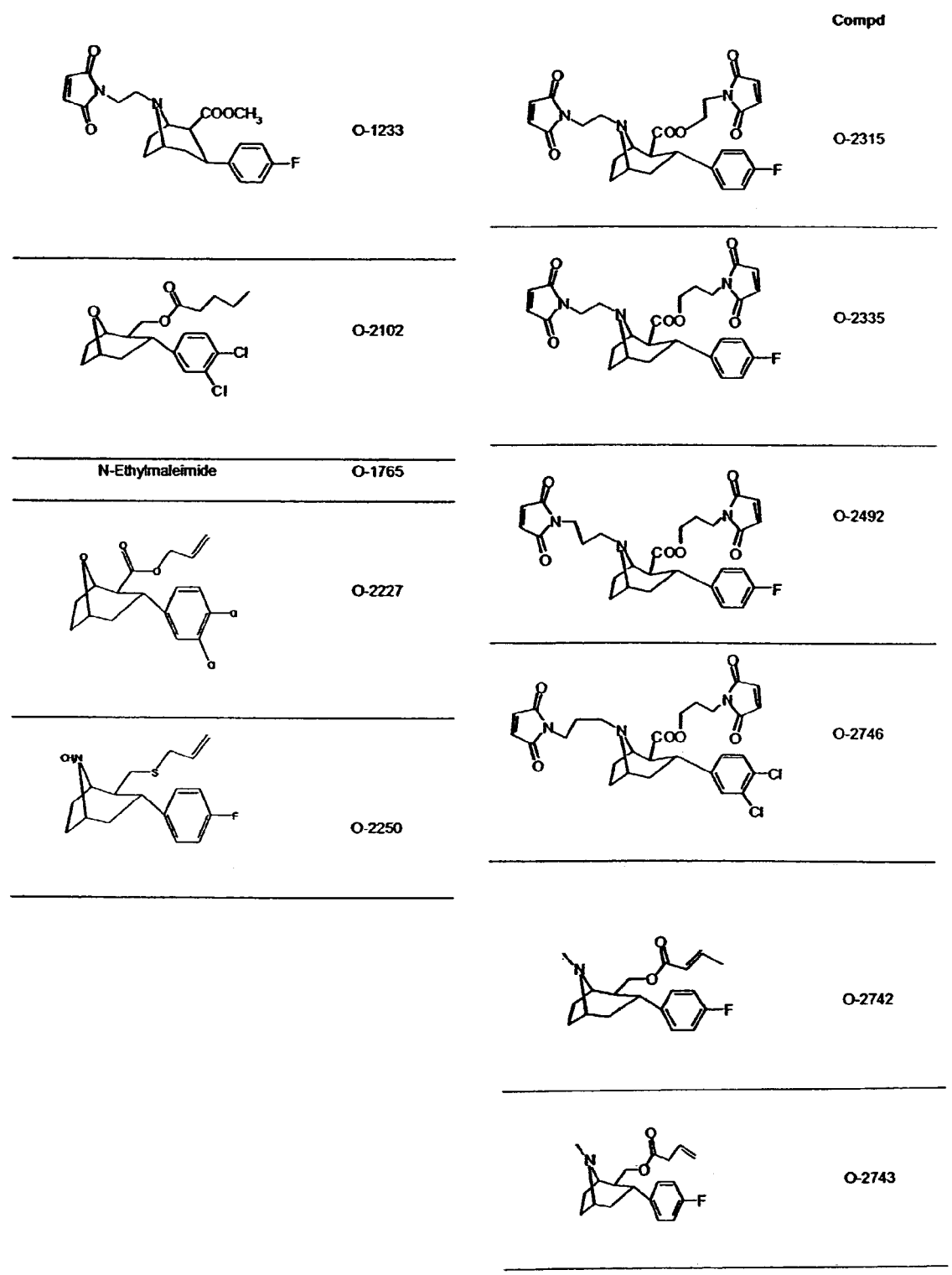
Figure 3C:
Figure 3C:
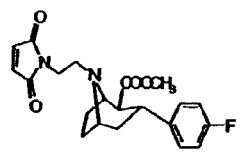
Figure 3C:
Figure 3C:
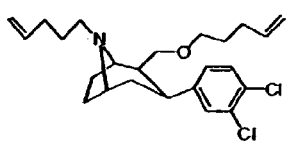
Figure 3C:
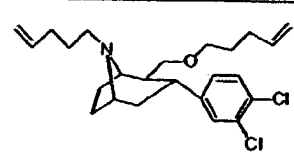
Figure 3C:
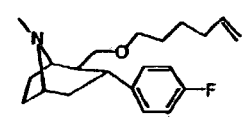
Figure 3C:
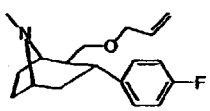
Figure 3C:
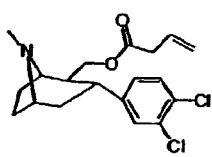
Figure 3C:
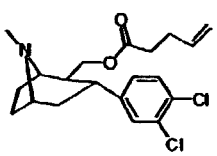
Figure 3C:
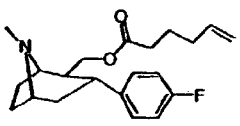
Figure 3C:
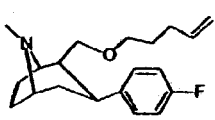
Figure 3C:
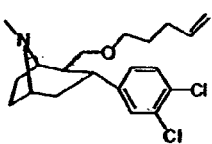

The synthesis of exemplary compounds was accomplished as outlined in Schemes 1 and 2 (FIGS. 1 and 2). See Meltzer, P. et al., *Bioorg. Med. Chem.* 10 (2002), incorporated herein in its entirety. The approaches presented below are generally applicable for substituted compounds in the 8-oxa, 8-aza and 8-carba series. Synthetic routes for the 8-carba series are similar to those for the 8-oxa series (Meltzer et al., *J. Med. Chem.*, 43:2982-2991 (2000)).

The 8-oxabicyclo[3.2.1]oct-2-ene (Meltzer et al. *J. Med. Chem.* 2661, 1997) served as precursor for both the 3α-aryl and 3β-aryl in the 8-oxa series. Scheme 1 (FIG. 1) exemplifies 3α- and 3β-(3,4-dichlorophenyl)-8-oxa compounds. Reagents and conditions: (i) Na(TMS)2N, Ph(Tf)2N, THF, −78° C.; (ii) ArB(OH)2, Pd2dba3, Na2CO3, LiCl; (iii) SmI2, methanol, −78° C.; (iv) LAH, THF, 100%; (v) Et3N, RCOCl, 51%; (vi) THF, NaH, RBr, 30%; (vii) RCOCl, Et3N, CH2Cl2, 12%; (viii) Et3N, RCOCl, CH2Cl2, 76%; (ix) mCPBA, CH2Cl2, 54%. Thus reduction of the 2,3-ene provides both the 3α-aryl and 3β-aryl compounds (shown as 1). The 3α-aryl compound 4 was used here since 3α-aryl compounds are more DAT selective than are the 3α-aryl analogs. Reduction of the ester with lithium aluminum hydride in THF then provides the alcohol 2. Reaction of the alcohol, under basic conditions with selected acid chlorides and alkyl or alkenyl bromides, then provides the esters 3-5 and ether 6 in good yield. The epoxide 7 is obtained by oxidation of the unsaturated compound 3 with m-chloroperbenzoic acid (mCPBA).

The 8-azabicyclo[3.2.1]oct-2-ene (Meltzer et al. *J. Med. Chem.* 855, 1993) served as precursor for both the 3α-aryl and 3β-aryl in the 8-aza series. Scheme 2 (FIG. 2) exemplifies 3α and 3β-(4-fluorophenyl)-8 aza compounds. Reagents and conditions: (i) Na(TMS)2N, Ph(Tf)2N, THF, −78° C.; (ii) ArB(OH)2, Pd2dba3, Na2CO3, LiCl; (iii) SmI2, methanol, −78° C.; (iv) LAH, THF, 100%; (v) Et3N, RCOCl, 51%; (vi) THF, NaH, RBr, 30%; (vii) RCOCl, Et3N, CH2Cl2, 12%; (viii) Et3N, RCOCl, CH2Cl2, 76%; (ix) mCPBA, CH2Cl2, 54%. Thus reduction of the 2,3-ene provides both the 3α-aryl and 3β-aryl compounds (shown as 9 and 10). Demethylation was accomplished with ACE chloride (α-chloroethylchloroformate). Alkylation, generally in the presence of potassium iodide and potassium carbonate in dry acetonitrile, was then achieved with appropriate alkyl bromides to provide the targets 12-15.

The invention also features pharmacological uses for the above-described compounds to affect monoamine transport and to affect receptor function. For example, the compounds can be used as medications to control cocaine dependence. They are useful not only for treating cocaine and other substance dependence, but also they are useful generally for treating neuropsychiatric disorders and medical disorders associated with monoamine uptake and receptor systems, such as, but not limited to, attention deficit hyperactivity disorder, depression, obsessive compulsive disorder and Parkinson's disease.

For use in the present invention, the compounds of interest can be made into pharmaceutical compositions, comprising the desired compounds in a pharmaceutically acceptable carrier. Pharmaceutically acceptable carriers are well known to those skilled in the art. An exemplary pharmaceutical composition is a therapeutically effective amount of a compound of the invention optionally included in a pharmaceutically-acceptable and compatible carrier. The term "pharmaceutically-acceptable and compatible carrier" as used herein, and described more fully below, refers to e.g., one or more compatible solid or liquid filler diluents or encapsulating substances that are suitable for administration to a human or other animal. The route of administration can be varied but is principally selected from intravenous, nasal and oral routes. For parenteral administration, e.g., it will typically be injected in a sterile aqueous or non-aqueous solution, suspension or emulsion in association with a pharmaceutically-acceptable parenteral carrier such as physiological saline.

The term "therapeutically-effective amount" is that amount of the pharmaceutical compositions which produces a desired result or exerts a desired influence on the particular condition being treated.. Various concentrations may be used in preparing compositions incorporating the same ingredient to provide for variations in the age of the patient to be treated, the severity of the condition, the duration of the treatment and the mode of administration. An effective dose of the compound is administered to a patient based on $IC_{50}$ values determined in vitro.

The term "compatible", as used herein, means that the components of the pharmaceutical compositions are capable of being commingled with the compounds of the present invention, and with each other, in a manner such that there is no interaction that would substantially impair the desired pharmaceutical efficacy.

Dose of the pharmaceutical compositions will vary depending on the subject and upon particular route of administration used. Pharmaceutical compositions of the present invention can also be administered to a subject according to a variety well-characterized protocols.

The pharmaceutical composition may a liquid composition in pyrogen-free, sterilized container or vial. The container can be unit dose or multidose.

The invention also relates to methods of screening for candidates for use as partial antagonists for transporter systems. To screen candidate compounds, dopamine transport containing cells are preincubated with the compound so that a reaction with the transporter occurs. After a later, secondary reaction, the contrasting effect of the drug on cocaine binding compared to dopamine transport indicates a positive result. While not essential to successfully practicing the invention and without limiting us to a single mechanism, it is believed that the following can occur in some embodiments of the invention. After cleavage and release of the target ligand, the barb remains in place so that dopamine reuptake is permitted, while cocaine binding continues to be inhibited by the barb. A pronounced reduction of [$^3$H]cocaine binding and relative sparing of [$^3$H] dopamine transport demonstrates a lower abuse liability than cocaine. Screens to identify candidate compounds are discussed below.

This invention will be illustrated further by the following examples. These examples are not intended to limit the scope of the claimed invention in any manner. The Examples provide suitable methods for preparing compounds of the present invention. However, those skilled in the art may make compounds of the present invention by any other suitable means. As is well known to those skilled in the art, other substituents can be provided for the illustrated compounds by suitable modification of the reactants.

Screening

To screen candidate compounds, HEK-293 cells stably transfected with the human dopamine transporter cDNA are preincubated either with vehicle or with the compound being evaluated (e.g., O-1893). Within one hour of preincubation with the drug, during which a theoretical chemical reaction with the transporter occurs, a near total loss of [$^3$H]cocaine binding (DPM) was observed, but a partial sparing of [$^3$H] dopamine transport was observed. Initially, transporter affinity for dopamine was reduced (n=3). During the 24 hours, after a theoretical secondary chemical reaction occurred, the contrasting effects of O-1893 on these parameters persists. [$^3$H]Cocaine binding (CDPM) was reduced more than 50% whereas [$^3$H] dopamine transport was reduced to a lesser extent (n=4). The pronounced reduction of [3H]cocaine binding and relative sparing of [$^3$H]dopamine transport demonstrates the feasibility of developing a partial cocaine antagonist that may display lower abuse liability than cocaine. Studies in primates can be used for pre-clinical evaluation.

Experimental Section

NMR spectra were recorded in CDCl3 on a JEOL 300 NMR spectrometer operating at 300.53 MHz for $^1$H, and 75.58 MHz for $^{13}$C. Tetramethylsilane (TMS) was used as internal standard. Melting points are uncorrected and were measured on a Gallenkamp melting point apparatus. Thin layer chromatography (TLC) was carried out on Baker Si250F plates. Visualization was accomplished with either UV exposure or treatment with phosphomolybdic acid (PMA). Flash chromatography was carried out on Baker Silica Gel 40 mM or by radial chromatography on a Chromatotron. Elemental analyses were performed by Atlantic Microlab, Atlanta, Ga. All reactions were conducted under an inert ($N_2$) atmosphere. Coupling constants (J) are reported in Hz.

EXAMPLE 1

[3α(3,4-dichlorophenyl)-8-oxabicyclo[3.2.1]oct-2β-yl]methanol (2)

Lithium aluminum hydride (LAH) (3.64 g, 96 mmol) was cooled to 0° C. in anhydrous THF (40 mL), 2β-Carbomethoxy-3α-(3,4-dichlorophenyl)-8-oxabicyclo[3.2.1] octane, 1 (Meltzer et al. J. Med. Chem. 2661, 1997) (8.0 g, 25.4 mmol) was dissolved in THF (60 mL) and added dropwise to the stirred reaction mixture. The reaction was warmed to ambient temperature and stirred for 18.5 h. The slurry was cooled to 0° C. and the excess LAH was slowly decomposed by addition of water (25 mL) and refluxing for 20 min. The mixture was filtered and the solid collected was rinsed with ether. The filtrate was dried ($MgSO_1$), filtered and condensed in vacuo to a viscous clear oil (7.3 g, ca. 100%). A portion of the. clear oil was purified by crystallization (methylene chloride/hexanes) yielding clear, colorless cubic crystals. Mp 75-76° C.; $^1$H NMR δ 7.36 (d, 1H, J=8.3), 7.31 (d, 1H, J=22), 7.06 (dd, 1H, J=2.2, 8.3), 4.44 (dt, 2H, J=2.8, 8.3), 3.53 (dt, 2H, J=2.8, 6.4), 2.61 (m, 1H), 2.36 (m, 1H), 2.22-2.14 (m, 1H), 2.11-1.90 (m, 1H), 1.75-1.62 (m, 3H), 1.47 (dt, 1H, J=4.6, 5.2), 1.33 (ddd, 1H, J=2.8, 11.0, 13.8); $^{13}$C NMR δ 144.79, 132.24, 130.22, 130.04, 129.65, 127.32, 74.56, 71.90, 64.61, 51.02, 37.61, 35.19, 31.89, 30.78.

EXAMPLE 2

Pent-4-enoic acid-(3α-(3,4-dichlorophenyl)-8-oxabicyclo[3.2.1]oct-2β-yl)lmethyl ester (3) (O-1893)

The crude alcohol 2 (5.44 g, 18.9 mmol) was stirred with dry triethylamine (5 mL) in anhydrous methylene chloride (75 mL) under a nitrogen atmosphere. Pentenoyl chloride (2.6 mL, 23.7 mmol) was added slowly via syringe. The reaction mixture was stirred for 15.5 h, filtered through a pad of silica and concentrated under vacuum to yield an orange oil. The crude product was purified by radial chromatography (6 mm, 20% ether/hexanes) to give a yellow oil (6.71 g, 96%).

Rf 0.63 (20% ethyl acetate/hexanes). A portion of the crude oil (3.71 g, 10.0 mmol) was crystallized from hexanes to yield clear, colorless crystalline plates (1.91 g, 27%). Mp 49-50° C.; $^1$H NMR δ 7.34 (d, 1H, J=8.3), 7.29 (d, 1H, J=2.2), 7.04 (dd, 1H, J—2.2, 8.3), 5.89-5.72 , (m, 1H), 5.01 (ddd, 2H, J=1.6, 8.8, 17.3), 4.45 (ddd, 1H, 2.48, 6.33, 8.8), 4.26 (d, 1H, J=7.7), 3.95 (d, 2H, J=6.1), 2.61 (m, 1H), 2.40-2.30 (m, 4H), 2.22-1.91 (m, 2H), 1.84-1.80 (m, 1H), 1.73-1.63 (m, 2H), 1.30 (ddd, 1H, J=2.5, 11.3, 13.8); $^{13}$C NMR δ 172.96, 144.17, 136.52, 132.43, 130.38, 130.34, 129.69, 127.33, 115.53, 74.24, 66.31, 47.98, 38.14, 35.99, 33.33, 31.99, 30.94, 28.71. Anal. ($C_{19}H_{22}O_3Cl_2$) C,H.

EXAMPLE 3

3-Methylbutanoic acid-[3α-(3,4-dichlorophenyl)-8-oxabicyclo[3.2.1]oct-2β-yl]methyl ester (4) (O-2059)

The alcohol 2 (1.0 g, 3.48 mmol) was dissolved in dry methylene chloride (20 mL) and treated with triethylamine (1.0 mL, 7.2 mmol) and i-valeryl chloride (0.52 mL, 4.29 mmol). The reaction solution was stirred under nitrogen atmosphere at room temperature for 16 h. It was then diluted with methylene chloride (50 mL) and extracted with saturated sodium bicarbonate solution (50 mL) and brine (50 mL). The organic phase was condensed to a yellow oil which was purified by radial chromatography (6 mm plate, 10-20% ethyl acetate/hexanes) to give a clear, colorless oil (0.98 g, 76%). $R_f$ 0.40 (20% ethyl acetate/hexanes); $^1$H NMR δ 7.37 (d, 1H, J=8.3), 7.29 (d, 1H, J=2.2), 7.06 (dd, 1H, J 2.2, 8.3), 4.44 (ddd, 1H, J=2.5, 6.3, 8.8), 4.27 (d, 1H, J=7.7), 3.92 (d, 2H, J=6.1), 2.62 (dt, 1H, J=6.9, 11.0), 2.40-2.30 (m, 1H), 2.20-1.80 (m, 4H), 1.80-1.75 (m, 1H), 1.75-1.58 (m, 2H), 1.3-1.20 (m, I H), 0.91 (d, 6H, J=6.3); $^{13}$C NMR δ 172.97, 144.13, 132.34, 130.32, 130.24, 129.66, 127.27, 74.23, 71.69, 65.98, 47.95, 43.18, 38.14, 35.92, 31.94, 30.91, 25.53, 22.31. Anal. ($C_{19}H_{24}O_3Cl_2$) C, H, Cl.

EXAMPLE 4

Pentanoic acid-[3α-(3,4-dichlorophenyl)-8-oxabicyclo[3.2.1]oct-2β-yl]methyl ester (5) (0-2102)

The crude alcohol 2 (0.70 g, 2.43 mmol) was dissolved in dry methylene chloride (20 mL) and treated with triethylamine (1.0 mL, 7.2 mmol) and valeryl chloride (0.6 mL, 5.1 mmol). The reaction solution stirred under nitrogen atmosphere at room temperature for 16 h. It was then diluted with methylene chloride (50 mL) and extracted with saturated sodium bicarbonate solution (50 mL) and brine (50 mL). The organic phase was condensed and purified by radial chromatography (2 mm plate, 10% ethyl acetate/hexanes) to give a clear, colorless oil (0.70 g, 78%). The oil was crystallized from hexanes to yield clear, colorless crystals (0.11 g, 12%). R 0.50 (20% ethyl acetate/hexanes). Mp 26° C.; $^1$H NMR δ 7.36 (d, I H, J=13.3), 7.29 (d, 1H, J=2.2), 7.06 (dd, 1H, J=2.2, 8.3), 4.44 (ddd, 1H, J=2.5, 6.6, 8.8), 4.27 (d, 1H, J=7.7), 3.95 (d, 2H, J=6.1), 2.59 (dt, I H, J=4.0, 6.9), 2.39-2.29 (m, 1H), 2.24-1.46 (m, 9H), 1.36-1.22 (m, 3H), 0.89 (t, 3H, J=7.2); $^{13}$C NMR δ 173.66, 144.15, 132.29, 130.27, 130.17, 129.62, 127.24, 74.16, 71.67, 66.08, 47.87, 38.07, 35.95, 33.76, 31.90, 30.84, 26.82, 22.12, 13.59, Anal.($C_{19}H_{24}Cl_2O_3$) C, H.

EXAMPLE 5

3α-(3,4-Dichlorophenyl)-2β-pent-4-enyloxyxmethyl-8-oxabicyclo[3.2.1]octane (6) (O-2153)

The alcohol 2 (200 m, 0.69 mmol) and 5-bromo-1-pentene (114 mg. 0.76 mmol) were mixed in anhydrous THF (20 mL) at room temperature under nitrogen atmosphere. Sodium hydride (113 mg, 60% in mineral oil, 2.82 mmol) was added. The resulting solution was heated at reflux for 3.5 h. The reaction solution was cooled and water (40 mL was added. This was extracted with methylene chloride (2×50 mL). The extracts were dried ($Na_2SO_4$), combined and evaporated. The residue was purified by flash column chromatography yielding a light yellow oil (74 mg, 30%). R 0.32 (30% ethyl acetate/hexanes); $^1$H NMR δ 7.35 (d, 1H), 7.29 (d, 1H), 7.04 (dd, 1H), 5.85-5.72 (m, 1H), 5.03-4.92 (m, 2H), 4.45-4.36 (m, 2H), 3.39-3.28 (m, 2H), 3.26-3.16 (m, 2H), 2.59-2.49 (m, 1H), 2.37-2.29 (m, I H), 2.18-2.03 (m, 3H), 2.00-1.92 (m, 1H), 1.74-1.58 (m, 5H), 1.32-1.22 (m, 1 1-1). $^{13}$C NMR δ 145.01, 138.25, 132.27, 130-24, 130.05, 129.81, 127.40, 114.69, 71.80, 72.77, 71.73, 70.51, 49.38, 38.29, 35.79, 32.17, 30.98, 30.29, 28.73. Anal. ($C_{19}H_{24}Cl_2O_2$) C, H, Cl.

EXAMPLE 6

3-Oxiranyl-propionic acid [3α-(3,4-dichlorophenyl)-8-oxabicyclo[3.2.1]oct-3β-yl]methyl ester (7) (0-1834)

Alkene 3 (3.4 g, 9.2 mmol) in dry methylene chloride (100 mL) was treated with mCPBA and stirred at ambient temperature for 19.5 h. Excess mCPBA was quenched with $Na_2S_2O_3$ (3 g) and stirred with water (100 mL). The two phases were separated, and the organic phase was washed with saturated sodium bicarbonate (2×100 mL). The aqueous phase was back extracted with methylene chloride, then the combined organic layers were dried ($MgSO_4$), filtered and condensed in vacuo to a yellow oil (4 g crude). The crude product was purified by radial chromatography (6 mm, 20-30% ethyl acetate/hexanes) to give a pale yellow oil (1.90 g, 54%). Rf 0.22 (30% ethyl acetate/hexanes); $^1$H NMR δ 7.37 (d, 1H, J=8.3), 7.28 (d, 1H, J=2.2), 7.05 (dd, 1H, J=2.2, 8.3), 4.45 (ddd, 1H, J=2.5, 6.3, 8.8), 4.25 (d, 1H, J=7.43), 3.95 (d, 2H, J=6.0), 2.94, (ddd, 1H, J=3.0, 6.9, 9.6), 2.75 (dd, 1H, J—4.7, 4.1), 2.59 (dt, 1H, J=6.9, 10.6)2.49 (dd, 1H, J=4.7, 5.0), 2.39-2.30 (m, 3H), 2.20-2.08 (m, 1H), 2.00-1.75 (m, 3H), 1.76-1.60 (m, 3H), 1.29 (ddd, 1H, J—2.5, 11.3, 13.8); $^{13}$C NMR δ 172.75, 144.16, 132.44, 130.40, 130.35, 129.69, 127.34, 74.20, 71.79, 66.53, 51.12, 41.98, 46.97, 38.11, 36.04, 32.01, 30.93, 30.19, 27.44. Anal. ($C_{19}H_{22}O_4Cl_2$) C, H.

EXAMPLE 7

1-Bromo-3-(methoxyacetoxy)n-propane

1-Bromopropan-3-ol (1.32 mL, 14.6 mmol) was dissolved in anhydrous methylene chloride and cooled to 0° C. under nitrogen atmosphere. The solution was treated with triethylamine (2.2 mL, 15.8 mmol) and methoxyacetyl chloride (1.42 mL, 15.5 mmol) then warmed to room temperature. The reaction mixture was stirred for 17.5 h. It was then diluted with methylene chloride (150 mL) and extracted with saturated sodium bicarbonate (2×50 mL). The aqueous phase was back extracted with methylene chloride (100 mL) and the organic phases were combined and concentrated in vacuo to yield a crude, pale yellow oil (3.27 g). $^1$H NMR δ 4.25 (t, 2H, J=6.1), 4.05 (s, 2H), 3.45 (s, 3H), 3.22 (t, 2H, I=6.9), 2.18 (quint, 2H, J=6.6). The product was used as such in the following reaction.

EXAMPLE 8

(1R) 2β-Carboxymethyl-3β-(4-fluorophenyl)-8-methyl-8-azabicyclo[3.2.1]octane, 9 and (1.R) 2β-carboxymethyl-3α-(4-fluorophenyl)-8-methyl-8-azabicyclo[3.2.1]octane, 10

To a solution of $SmI_2$ (2.6 L, 0.1M in THF) was added a solution of 8 (18.8 g, 63 mmol) in THF (anhydrous, 142 mL) dropwise at −78° C. under nitrogen, the mixture was stirred for 45 min after the addition. Anhydrous methanol (142 mL) was then added to the solution, and the reaction mixture was stirred to another 2 h. The reaction was quenched with TFA (73 mL) at −70° C., and water (1.5 L) was added and the reaction mixture was allowed to warm to room temperature slowly. The mixture was then made basic with $NH_4OH$ to pH=10 and filtered through Celite; the Celite was washed with ethyl ether. The filtrate was saturated with sodium hydrogen sulfite and the layers separated. The ether layer was washed with brine, dried over $Na_2SO_4$, filtered and concentrated to dryness. The crude product was purified by flash chromatography (silica gel 1:40, 95%, o EtOAc/hex (2:8)+ 5% TEA, 95% EtOAc/hex (6:4)+5% TEA) to yield a white solid of a 1:1 mixture of 9 and 10 (15.9 g, 91%). These epimers were separated by gravity chromatography (silica gel 1:55, 3% $EtOH/CHCl_3$, 95% EtOAc/hex(2:8)+5% TEA). Two products were obtained:

(2) White solid, 10 (6.22 g, 36%), Rf=0.35 in 95% EtOAc/hex (2:8)+5% TEA, mp.48.0-48.9° C. $^1H$ NMR δ 7.24-7.19 (m, 2H), 6.95 (tt, 2H, J=8.8, 2.3),3.56-3.54 (m, 1H), 3.50 (s, 3H), 3.38-3.36 (m, 1H), 2.97 (dt, 1H, J=12.7, 5.3), 2.86 (t, 1H, J=3.9),2.56 (td, 1H, J=12.7, 2.9), 2.23 (s, 3H), 2.20-2.08 (m, 2H), 1.76-1.61 (m, 3H).

(2) White solid, 9 (2.7 g, 16%), R=0.35 in 95% EtOAc/hex (2;8)+5% TEA, mp.90.5-91.5° C.
$^1H$ NMR δ 7.18-7.14 (m, 2H), 6.94 (tt, 2H, J=8.8, 2.3 Hz), 3.58 (s, 3H), 3.35-3.25 (m, 3H), 2.50-2.39 (m, 2H), 2.25 (s, 3H), 2.30-2.09 (m, 2H), 1.62-1.43 (m, 2H), 1.36-1.27 (m, 1H).

EXAMPLE 9

(1 R)-2β-Methoxycarbonyl-3α-(4-fluorophenyl)-8-azabicyclo[3.2.1]octane (11)

(1 R)-2 β-Methoxycarbonyl-3α-(4-fluorophenyl)-8-methyl-azabicyclo[3.2.1]octane (95 mg, 0.34 mmol) and 1-chloroethyl cbloroformate (ACE-Cl) (7 mL) were combined and heated at 100° C. (oil bath temperature) for 1 h. Excess ACE-Cl was then removed under reduced pressure and methanol (50 mL) was added to the residue. The mixture was then heated at reflux for 30 min and concentrated to dryness. The residue obtained was dissolved in $CH_2Cl_2$ (75 mL), washed with aqueous $NH_4OH$, dried over $Na_2SO_4$, filtered, and concentrated to afford the crude demethylated product. Purification by flash chromatography (0-5% $NH_4OH$, 10% MeOH in EtOAc) gave 86 mg (95%) of 11. Rf 0.66 (10% MeOH/ErOAc+0.5% $NH_4OH$); $^1H$ NMR δ 1.2 (ddd, 11-1), 1.2-2.8 (m, 5H), 3.3-3.6 (m, 2H), 3.5 (s, 3H), 3.8-4.2 (m, 2H), 6.9-7.3 (m, 4H).

EXAMPLE 10

2β-Carbomethoxy-3β-(4-fluorophenyl)nortropane (11)

2β-Carbomethoxy-3β-(4-fluorophenyl)tropane 9 (2.6 g, 9.38 mmol) and α-chloroethyl chloroformate (ACE-Cl) (7 mL, 68 mmol) were combined and heated at 100° C. (oil bath temperature) for 1 h. Excess ACE-Cl was then removed under reduced pressure and -methanol (50 mL) was added to the residue. The mixture was then heated at reflux for 30 min, and then concentrated to dryness. The residue obtained was dissolved in $CH_2Cl_2$ (75 mL), washed with saturated $NaHCO_3$ solution, dried over sodium sulfate, filtered and concentrated to afford the crude demethylated product (2.58 g). Purification by flash chromatography (10% $Et_3N/Et_2O$) gave 11 as a tan solid, 1.82 g; (74%): mp 115-116.5° C.; Rf 0.18 (i-$PrNH_2$: EtOAc; hexane::3:47:50); $^1H$ NMR δ 0.75-3.23) (m, 8H), 3.42 (s, 3H, $OCH_3$), 3.75 (m, 3H), 6.78-7.38 (m, 414, ArH). Anal. ($C_{15}H_{18}NO_2F$) C, H, N.

EXAMPLE 11

2β-Carbomethoxy-3β-(4-fluorophenyl)-8-(3-methoxyacetoxypropyl)-8-azabicyclo[3 2.1]octane (12) (0-1071)

1-Bromo-3-(methoxyacetoxy)propane (2.7 g, 12.8 mmol) in anhydrous acetonitrile (100 mL) was added to a dried mixture of 2β-carbomethoxy-3β-(4-fluorophenyl)-8-azabicyclo[3.2.I]octane, 11 (Meltzer et al, J. Med. Chem. 855, 1993) (3.1 8, 11.8 mmol), potassium iodide: (1.70 g, 10.2 mmol) and potassium carbonate (fine mesh, 5.86 g, 42.4 mmol). The slurry was refluxed for 20 h while stirring vigorously. The reaction mixture was concentrated to dryness in vacuo and the residue was dissolved in ethyl acetate (100 mL). The mixture was filtered through a pad of silica, rinsed with ethyl acetate and the combined filtrate was condensed. The product was purified by column chromatography (30-50% ethyl acetate/hexanes) to yield an orange oil (2.35 g. 51%). Rf 0.20 (30% ethyl acetate/hexanes+0.5 mL triethylamine/mL eluent). $^1H$ NMR δ 7.24-7.14 (dd, J=5.5, 8.8, 2H), 6.97-6.91 (dd, J=8.5, 8.8, 2H), 4.31-4.16 (m, 2H), 4.02 (s, 2H), 3.66 (bs, 1H), 3.48 (s, 3H), 3.44 (s, 3H), 3.38 (bs, 1H), 2.98 (dt, 1H, J=5.0, 102), 2.88 (dd, 1H, J=3.9, 4.1), 2.55 (dt, 1H, J=3.0, 12.4), 2.40-2.24 (m, 2H), 2.19-1.90 (m, 2H), 1.81-1.58 (m, 5H); $^{13}C$ NMR δ 171.80, 170.14, 162.52, 159.30, 138.63, 128.62, 114.56, 114.29, 69.66, 63.06, 63.00, 61.31, 59.18, 52.83, 50.86, 49.93, 34.08, 33.44, 28.09, 25.84, 25.79. Anal. ($C_{21}H_{25}O_5NF$) C, H, N.

EXAMPLE 12

2β-Carbomethoxy-3β-(4-fluorophenyl)-8-(2-acetoxyethyl)-8-azabicyclo[3.2.1]octane (13) (O-1103)

2β-Carbomethoxy-3β-(4-fluorophenyl)-8-azabicyclo [3.2.1]octane, 11 (4.79 g, 18.2 mmol) was combined with potassium iodide (3.20 g, 19.3 mmol), potassium carbonate (12.8 g, 92.5 mmol), dry acetonitrile (100 mL) and (2-bromoethyl)acetate (2.0 mL, 18.1 mmol) and the slurry was brought to reflux for 6 h. The reaction mixture was condensed directly, taken up in ethyl acetate and filtered through a pad of silica. The filtrate was condensed and the crude residue was purified by radial chromatography (6 mm plate, 20% ethyl acetate, 5% triethyl amine, 75% hexanes). Rf 0.43 (20% ethyl acetate, 5% triethyl amine, 75% hexanes) to yield a clear gold oil (3.24 g, 51%). $^1$H NMR δ 7.20 (dd, 2H, J=5.5, 8.5), 6.97 (dd, 2H, J=8.5, 8.8),=4.22-3.98 (m, 2H), 3.76-3.70 (m, 1H), 3.49 (s, 3H), 3.43 (bs, 1H), 3.20-2.92 (m 1H), 2.92-2.86 (bt, 1H, J=3.7), 2.62-2.42 (m, 3H), 2.20-1.92 (m, 5H), 1.82-1.60 (m, 3H); $^{13}$C NMR δ 171.61, 170.95, 162.75, 159.34, 138.60, 128.69, 128.59, 114.67, 114.39, 63.69, 63.47, 61.91, 52.72, 52.20, 50.92, 34.05, 33.41, 26.00, 25.79, 20.91. Anal. ($C_{19}H_{24}O_4NF$ ⅓$H_2O$) C, H, N.

EXAMPLE 13

2-Bromoethyl pent-4-enoate

4-Pentenoyl chloride (2.8 mL, 25.4 mmol) was dissolved in anhydrous methylene chloride (50 mL) and cooled to 0° C. under nitrogen. 2-Bromoethanol (2.0 mL, 28.2 mmol) and triethylamine (3.8 mL, 27.3 mmol) was added to the reaction solution resulting in a thick yellow slurry. The reaction solution was stirred for 19.5 h while slowly warming to 22° C. The reaction mixture was diluted to 100 mL with methylene chloride and extracted with 75 mL of each of the following: water, sat. ammonium chloride, and sat. sodium bicarbonate. The organic phase was dried ($MgSO_4$), filtered and condensed in vacuo to yield a yellow oil (5.2 g cu. 100%) which was used as is for the next step. $^1$H NMR δ 5.90-5.65 (m, 1H), 5.15-4.90 (m, 2H), 4.39 (t, 2H, J=6.0), 3.48 (t, 2H, J=6.0), 2.50-2.30 (m, 4H).

EXAMPLE 14

2-Bromoethyl-3-oxiranylpropionate mCPBA (ca. 50% purity, 10.7 g, ca. 31.0 mmol) was with methylene chloride (50 mL) to dissolve. The solution was dried (Mg, $SO_4$) and filtered to remove magnesium salts and contaminating mCPBA. The filtrate was slowly added to the ester prepared above (5.2 g, 25.1 mmol) cooled to 0° C. The reaction mixture was then diluted with anhydrous methylene chloride (50 mL) and stirred under nitrogen for 20 h. The reaction mixture was then stirred vigorously with saturated sodium sulfite solution for 20 min, then treated with saturated sodium bicarbonate portionwise (3×25 mL). The mixture was stirred for 15 min then separated and the aqueous phase was extracted with methylene chloride (100 mL). The combined organic layers were washed with saturated sodium sulfite (75 mL), saturated sodium bicarbonate (75 mL), dried ($MgSO_4$) and filtered through a pad of silica, rinsing with methylene chloride. The filtrate was condensed to a clear gold oil (5.27 g, 93%), $^1$H NMR δ 4.42 (t, 2H, J=6.0), 3.51 (t, 2H, J=6.0), 3.01 (m, 1H), 3.80 (t, 1H, J=4.4), 2.54-2.50 (m, 3H), 2.10-1.95 (m, 1H), 1.80 (sextet, 1H, J=6.9). $^{13}$C NMR δ: 63.86, 51.16, 47.04, 30.18, 28.93, 27.45.

EXAMPLE 15

2β-Carbomethoxy-3β-(4-fluorophenyl)-8-[2-(3-oxiranylpropionyloxy)ethyl]-8-azabicyclo[3.2.1]octane (14) (O-1899)

A mixture of 2β-carbomethoxy-3β-(4-fluorophenyl)-8-azabicyclo[3.2.1]octane, 11 (504 mg, 1.91 mmol), potassium iodide (497 mg, 2.99 mmol) and potassium carbonate (2.63 g, 19.0 mmol) was placed in a flame-dried flask and treated with a solution of 2-bromoethyl-3-oxiranylpropionate (440 mg, 1.97 mmol) in anhydrous acetonitrile (20 mL). The mixture was brought to reflux and stirred for 7 h. The reaction was cooled and filtered through Celite and rinsed with ethyl acetate (3×50 mL). The filtrate was condensed and purified by radial chromatography (4 mm plate, 60% ethyl acetate/5% triethylamine/35% hexanes) to yield a pale orange oil (0.54 g, 67%). Rf 0.18 (30% ethyl acetate/1% triethylamine/69% hexanes); $^1$H NMR δ 7.20 (dd, 2H, J=5.5, 8.8), 6.95 (dd, 8.5, 8.8), 4.1 (dq, 2H, J=6.3, 11.3), 3.73 (bs, 1H), 3.48 (s, 3H), 3.42 (bs, 1H), 3.04-2.92 (m, 2H), 2.88 (br, 1H, J=4.0), 2.79 (t, 1H, J=4.7), 2.62-2.42 (m, 6H), 2.20-1.90 (m, 3H), 1.84-1.59 (m, 4H); $^{13}$C NMR δ 172.72, 171.61, 162.77, 159.48, 138.62, 128.72, 128.72, 114.73, 114.45, 63.89, 63.54, 61.98, 52.76, 52.27, 51.21, 50.99, 47.05, 34.10, 33.44, 30.33, 27.54, 26.07, 25.83. Anal. ($C_{22}H_{28}O_5NF$) C, H, N.

EXAMPLE 16

2β-Carbomethoxy-3β-(4-fluorophenyl)-8-(2-maleimidoethyl)-8-azabicyclo[3.2.1]octane (15) (O-1233)

N-(2-Hydroxyethyl)maleimide (282 mg, 2 mmol) was dissolved in dichloromethane (50 mL) and cooled to 5° C. To this solution was added successively, by syringe, triethylamine (360 μL, 2.6 mmol) and trifluoromethanesulfonic anhydride (360 μL, 2.1 mmol). The solution was allowed to achieve room temperature and then stirred overnight. Dichloromethane (50 mL) was added and the resulting solution washed with water (4×50 mL), dried (sodium sulfate), filtered and concentrated. The viscous oil (400 mg, 73% [Note: this compound is not stable, even at low temperature under nitrogen and should only be prepared immediately before use]) was taken up in dichloromethane (1 mL) and added to a solution of 11 (131 mg, 0.48 mmol) in dichloromethane (2 mL). DMF (2 drops) and triethylamine (67 μL, 0.48 mmol) were then added and the solution stirred overnight at room temperature. Dichloromethane (20 mL) and a saturated solution of sodium bicarbonate (20 mL) were then added to the solution and the phases separated. The aqueous phase was extracted further with dichloromethane (3×10 mL) and then all organic phases combined and dried (sodium sulfate). The solids were filtered and the filtrate concentrated and chromatographed on a silica gel column (200 g $SiO_2$, eluent 2% triethylamine in a 50:50 mixture of ethyl acetate and hexanes, fractions 1-11, 7 mL volume each and fractions 12-30, 13 mL volume each). The product containing fractions (14-19) were combined and concentrated and the white solid washed with ether and dried in a vacuum oven overnight to give 143 mg, 77% of the title compound. Mp. 121-122° C.; Rf 0.5 (2% triethylamine in ether/hexanes 1:1); $^1$H NMR δ 7.18 (m, 2H), 6.93 (m, 2H), 6.68 (s, 2H), 3.68 (m, 1H), 3.30-3.60 (m, 3H), 3.40 (s, 3H), 2.93 (dt, 1H, J=12.6, 5.2), 2.83 (t, 1H, J=3.8), 2.27-2.53 (m, 3H), 1.90-2.14 (m, 2H), 1.56-1.80 (m, 3H); $^{13}$C NMR 171.3, 170.9, 161.0 (d, J=243), 138.6 (bs), 134.0, 123.7 (d, J=7.5), 114.6 (d, J=20.8), 64.6, 59.5, 52.8, 50.92, 50.86, 36.7, 33.7, 33.5, 26.6, 25.3. Anal, ($C_{21}H_{23}FN_2O_4$) C,H,N.

TABLE 1

| Compound | Calculated | | | | Found | | | |
|---|---|---|---|---|---|---|---|---|
|  | C | H | N | Cl | C | H | N | Cl |
| O-1899 | 65.17 | 6.96 | 3.45 |  | 64.98 | 6.94 | 3.48 |  |
| O-1103 + 20 mol % H2O | 64.48 | 6.98 | 3.96 |  | 64.21 | 7.00 | 3.90 |  |
| O-1071 | 64.11 | 7.17 | 3.56 |  | 7.28 | 64.09 | 3.48 |  |
| O-1893 | 61.8 | 6.0 |  |  | 61.98 | 5.97 |  |  |
| O-2102 | 61.46 | 6.52 |  |  | 61.57 | 6.55 |  |  |
| O-2059 | 61.46 | 6.52 |  | 19.10 | 61.59 | 6.60 |  | 19.00 |
| O-1834 | 59.23 | 5.76 |  |  | 59.59 | 5.92 |  |  |

TABLE 1-continued

| Compound | Calculated | | | | Found | | | |
|---|---|---|---|---|---|---|---|---|
| | C | H | N | Cl | C | H | N | Cl |
| O-2153 | 64.23 | 6.81 | | 19.96 | 64.37 | 6.85 | | 19.73 |
| O-1233 | 65.27 | 6.00 | 7.25 | | 65.30 | 6.08 | 7.19 | |

Screening Compounds

The compounds are tested in HEK-293 cells transfected with the human dopamine transporter (hDAT cells). The cells robustly accumulate [$^3$H] dopamine and bind [$^3$H]cocaine. The prototype compound is O-1893. If hDAT cells are pre-incubated for 1 hour with O-1893, specific [$^3$H]cocaine binding sites decline approximately 90% but [$^3$H]dopamine transport decreases by 67%. After a 24 hour incubation with O-1893 (1 uM), [$^3$H]cocaine binding sites decline approximately 58% but [$^3$H]dopamine transport decreases by only 5%. At a higher concentration of O-1893 (μm), the decreases are 62% and 23% respectively. O-2153 yielded similar data. Results are summarized in the tables below.

TABLE 2

1 HOUR PRE-INCUBATION WITH O-1893

| DRUG | Tot- NS (dpms) | [$^3$H]cocaine binding % of control | Dopamine Vmax | Dopamine transport % of control |
|---|---|---|---|---|
| O-1893 | 991 | 10 | 23.9 ± 2.5 | 43 |
| No drug | 9.983 | | 55.1 ± 3.3 | |
| O-1893 | 2,181 | 7 | 72.9 ± 7.7 | 27 |
| No drug | 31,411 | | 266.2 ± 15.1 | |
| O-1893 | 1,624 | 12 | 23.7 ± 2.0 | 29 |
| No drug | 13,023 | | 82.4 ± 3.4 | |

Results: After 1 hour pre-incubation with O-1893, specific [$^3$H]cocaine binding sites decreased by 90%; 93%, 88%. In contrast [$^3$H]dopamine transport was reduced by 57%, 73%, 71%.

TABLE 3

24 HOUR PRE-INCUBATION WITH O-1893

| DRUG | Tot- NS (dpms) | [$^3$H]cocaine binding % of control | [$^3$H]Dopamine Transport Vmax | [$^3$H]Dopamine transport % of control |
|---|---|---|---|---|
| O-1893 | 4,913 | 42 | 126.5 ± 12.2 | 98 |
| No drug | 11,575 | | 129.3 ± 8.1 | |
| O-1893 | 6,331 | 49 | 164.5 ± 7.4 | 95 |
| No drug | 13,005 | | 172.8 ± 7.8 | |
| O-1893 | 3,154 | 45 | 47.6 ± 3.4 | 91 |
| No drug | 6,943 | | 52.3 ± 4.7 | |
| O-1893 | 3,853 | 43 | 77.5 ± 6.7 | 98 |
| No drug | 8,947 | | 79.5 ± 5.9 | |
| O-1893-2 | 32,199 | 65 | 127.3 ± 3.0 | 80 |
| No drug | 49,760 | | 159.5 ± 6.2 | |
| O-1893-2 | 11,740 | 30 | 90.9 ± 4.1 | 72 |
| No drug | 40,111 | | 126.2 ± 2.9 | |
| O-1893-2 | 8,903 | 39 | 82.5 ± 8.6 | 81 |
| No drug | 22,972 | | 101.7 ± 4.5 | |
| O-1893-2 | 8,060 | 32 | 161.2 ± 11.8 | 90 |
| No drug | 24,689 | | 179.6 ± 10.4 | |
| O-1893-2 | 12,986 | 49 | 78.0 ± 5.1 | 67 |
| No drug | 26,589 | | 115.9 ± 4.3 | |

Results: After 24 hour pre-incubation:

Specific [$^3$H]cocaine binding sites an average of 58% with 1 uM O-1893 and 62% with 5 uM (with different cells). In contrast, [$^3$H]dopamine transport is reduced by 5% with 1 uM O-1893 and 22% with 5 uM.

TABLE 4

24 HOUR PRE-INCUBATION WITH O-2153

| O-2153 | 12,216 | 28 | 151 ± 6.5 | 51 |
|---|---|---|---|---|
| No drug | 43,369 | | 294 ± 29.0 | |
| O-2153 | 6,792 | 18 | 89.6 ± 5.9 | 54 |
| No drug | 36,971 | | 165.2 ± 7.05 | |

Methods

Cell Plating Procedure:

HEK-293 cells stably transfected with the hDAT plasmid were grown at 5% $CO_2$ in a 37° C. water-jacketed incubator until ready to plate. Media of dishes with 90% confluency was aspirated off and cells were rinsed once with 6 ml cold PBS (4° C., pH 7.4). The rinse was aspirated and cells were harvested in 10 ml PBS and centrifuged for 5 minutes at 2,000 rpm. The cells were then resuspended in an appropriate amount of media and the suspension was stirred. Tissue culture plates coated with poly-D-lysine were prepared by adding 500 μl of media to each well and then 300 μl of cell suspension. Each well contained 800 ml of media and cells. Each plate was shaken vigorously to distribute cells evenly in wells and care was taken to keep the media in the wells. Cells were grown overnight in the incubator and were about 40-50% confluent the next day.

Pre-Incubation and Rinse Procedure:

Novel compounds were dissolved, if necessary in an appropriate concentration of EtOH and then at a concentration of 1 mM in 37° C. assay buffer consisting of Tris (5 mM), Hepes (8.5 mM), NaCl (120 mM), KCl (5.4 mM), $CaCl_2$ (1.2 mM), $MgSO_4$ (1.2mM), glucose (5 mM), and Tropolone (1 mM) at pH 7.4. The stock solution of 1 mM was diluted to 5-25 uM concentration. Cell buffer (pH 7.4 at 37° C.) containing the same final percentage of EtOH that was added to drug solution was set aside to add to the plates. The 24-well plates were removed from the incubator and 200 ul of novel drug or control buffer was added to each well to a total volume of 1 ml. Plates were then placed in the incubator and incubated for appropriate time periods (1 hour, 24 hours). At the end of the preincubation, cell plates were removed from the incubator and media aspirated by suction. Each well was rinsed 5 times and a final rinse with buffer (pH 7.4 at 25° C.) was made for 1-2 min in preparation for the assay.

Cocaine Binding Assay:

Serial dilutions of (−)cocaine, mazindol (10 uM), [$^3$H] cocaine (20 nM) were made. The buffer was aspirated, rinsed from the plate and [$^3$H]cocaine (200 ul) was added to each well, followed by (−)cocaine (200 ul) of the diluted stock, to a final total volume of 600 ul. Plates were incubated for 1 hour, the drug solution was aspirated, each well was rinsed once with 1 ml ice-cold cell buffer (pH 7.4 at 4° C.) and SDS was added to each well. After removing the SDS scintillation fluid was added and radioactivity was measured by liquid scintillation spectrometry.

Dopamine Uptake Assay:

Dopamine and mazindol were prepared in assay buffer (pH 7.4 at 37° C.). Serial dilutions of dopamine combined with 20 nM [$^3$H]dopamine, and mazindol were prepared to measure non-specific binding. Room temperature assay buffer was added to each well and buffer and mazindol were added to measure non-specific binding. In the dark, serially diluted [³H]dopamine was added, incubation proceeded for 10 minutes, the incubation medium was aspirated and each well rinsed with assay buffer. SDS was added to each well following aspiration of last rinse, removed, scintillation fluid added and radioactivity measured with liquid scintillation spectrometry.

The affinities ($IC_{50}$) of the compounds for the dopamine and serotonin transporters were determined in competition studies using [3H]2β-carbomethoxy-3β-(4-fluorophenyl)-8-methyl-8-azabicyclo[3.2.1]octane ([³H]WIN 35,428) to label the dopamine transporter and [³H]citalopram to label the serotonin transporter. Binding data for the compounds are presented in Table 5. Competition studies were conducted with a fixed concentration of radioligand and a range of concentrations of the test compound. All compounds inhibited [3H]WIN 35,428 and [³H]citalopram binding in a concentration-dependent manner. The six compounds inhibit [3H]WIN 35,428 binding to the DAT with nM potency (17-75 nM) and are reasonably selective versus the SERT (7-fold to 30-fold). In our assay of potential functional antagonism, the hDAT was incubated with each of the compounds 3-7 for a period of 24 hours. The cells were then exhaustively washed to remove non-covalently bound ligand and binding of cocaine (20 nM) and dopamine uptake (Vmax) were compared.

The controls, WIN 35,428 and (−)-cocaine, did not bind irreversibly to the DAT since inhibition of both DA uptake and cocaine binding after 24 hour incubation was 90% or more in both cases (Table 1). Therefore, washout was essentially complete. The compounds of this invention may be expected to have similar lipophilicity and were therefore expected to be washed out similarly. In contrast to WIN 35,428 and (−)-cocaine, the sulfhydryl acceptor, N-ethylmaleimide, did manifest irreversible binding within the same time frame (35% inhibition of both functions). The epoxide 7 showed a greater inhibition of dopamine reuptake than cocaine binding at 24 hours (68% versus 18%). Compounds 3 (racemic and enantiomerically pure (1R)-3) significantly inhibited cocaine binding to the DAT after 24 hours (63% and 80% respectively). However, inhibition of dopamine was much reduced. Unsaturated ether 6 manifested a preferred inhibition of cocaine binding to dopamine uptake (80% versus 40%) and therefore bound irreversibly and allowed substantial dopamine uptake. Saturated ester 3 showed no inhibition of binding or uptake; therefore no irreversible binding took place. In contrast, saturated ester 4 showed similar and substantial inhibition of DA uptake and cocaine binding after 24 hours (60%).

TABLE 5

Comparison of affinity of compounds for the dopamine transporter (DAT) and serotonin transporter (SERT) and the effects on dopamine transport and cocaine binding[a]

| Compound | Dopamine transporter $IC_{50}$ (nM) [³H]WIN 35,428 | Serotonin transporter $IC_{50}$ (nM) [³]citalopram | Selectivity SERT/ DAT | Inhibition of DA uptake after 24 h (%) | Inhibition of cocaine binding after 24 h (%) |
|---|---|---|---|---|---|
| WIN 35,428 | 11 | 160 | 15 | 2 | 12 |
| (−)-Cocaine[b] | 95 | 270 | 2 | | |
| N-Ethylmaleimide | >100,000 | >100,000 | — | 35 | 35 |
| 3, O-1893 (1R/S) | 20 | 593 | 30 | 23 | 63 |
| 3, O-2185 (1R) | 24 | 326 | 14 | 48 | 80 |
| 7, O-1834 | 17 | 292 | 17 | 68 | 18 |
| 6, O-2153 | 58 | 755 | 13 | 40 | 80 |
| 5, O-2102 | 71 | 917 | 13 | 0 | 0 |
| 4, O-2059 | 75 | 515 | 7 | 60 | 60 |

[a]Effects of 24-h pre-incubation of the test compounds on [³H]dopamine transport and [³H]cocaine (20 nM) bound in HEK-293 cells transfected with the human dopamine transporter. The cells were extensively washed prior to conducting binding and transport assays. Errors generally do not exceed 15% between replicate experiments. Highest doses tested were generally 10-100 μM. Results are expressed as % of control values and are the means of 2-5 determinations, each conducted in triplicate.
[b]Cocaine washes out completely within minutes. % refers to DPM of specifically bound (³H) cocaine to cells treated either with buffer or with compound.

TABLE 6

Binding of compounds at DAT and SERT.

| Compound | DAT | SERT | Incub Time | Inhibition of DA uptake | Inhibition of Cocaine Binding |
|---|---|---|---|---|---|
| O-2517 | 60 | | | | |
| O-2578 | 800 | | | | |
| O-2583 | 500 | | | | |
| O-2528 | 41 | | | | |
| O-1834 | 17 | 294 | 24 h | 68% | 18% |
| O-1103 | 20 | 200 | 24 h | 0% | 0% |
| O-1071 | 125 | 3,000 | 24 h | 0% | 0% |
| O-1899 | 53 | 230 | 24 h | 0% | 0% |
| | | | 48 h | 20% | 40% |
| O-1233 | 237 | 3,000 | | | 50%/1 h |
| O-1765 | | | 24 h | 35% | 35% |
| O-2227 | 3 | 32 | 1 h | 0% | 0% |
| | | | 24 h | 40% | 55% |
| O-2250 | 9 | 1,300 | 24 h | 35 | 50 |
| O-2315 | 2,000 | 14,000 | | | |
| O-2335 | 300 | 10,000 | | | |
| O-2492 | 237 | 2,000 | | | |
| O-2338 | 300 | | | | |
| O-2190 | 120 | 3,600 | | | |

While not wishing to be bound by theory, irreversible inhibition of the cocaine (but not dopamine) binding site by 3 on the DAT may occur as follows. The first step is non-covalent binding of the ligand 3 to the acceptor site on the DAT. Since the ligand is now tightly bound, this is followed by pseudointramolecular attack by the sulfhydryl radical of a proximal cysteine, upon the double bond, to provide the covalently bound DAT-ligand complex. This complex then undergoes cleavage of the ester and releases 2-hydroxmethyloxabicyclo [3.2.1]octane for washout from the acceptor site and the DAT itself. The remaining barb on the binding site now serves to differentially inhibit dopamine uptake and cocaine binding.

A number of embodiments of the invention have been described. Nevertheless, it will be understood that various modifications may be made without departing from the spirit and scope of the invention. Accordingly, other embodiments are within the scope of the following claims.

What is claimed is:

1. A compound consisting of
a) a ligand moiety for a monoamine transporter or receptor selected from dopamine, norepinephrine, and serotonin transporters or receptors wherein the ligand has the following Formula 1:

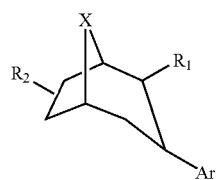

in which:
the 2-, 3-, 6-, or 7-positions are α or β;
the compounds are racemic or 1 R-or 1 S-configured;
X =CHR$_3$, CHR$_1$, CHW$_1$, CW$_1$W$_1$, NR$_3$, NR$_9$, NSO$_2$R$_3$, NSO$_2$R$_1$ or CX$_2$W, with the N or C atom being a member of the ring;
Ar =Phenyl or 1-naphthyl or 2-naphthyl, unsubstituted or substituted with one or more group selected from: —H; —Br; —Cl; —I; —F; —OH; —CH$_3$; —CF$_3$; —NO$_2$; —NH$_2$; —CN; —NHCOCH$_3$, —C(CH$_3$)$_3$, —C(CH$_3$) CH$_3$, (CH$_2$)$_q$CH$_3$, where q=0-6; —COCH$_3$; alkyl; alkenyl; alkynyl; allyl; isopropyl; isobutyl; wherein each substituent can be at the 2, 3 and/or 4 position of the ring;
W or X$_2$=H, OH, OCH$_3$, OAc, OCOR$_4$, CH$_3$, (CH$_2$)$_n$CH$_3$, R$_4$;
W$_1$=H, Br, Cl, I, F, OH, OCH$_3$, CF$_3$, NO$_2$, NH$_2$, CN, NHOOCH$_3$, N(CH$_3$)$_2$, (CH$_2$)$_n$CH$_3$, COCH$_3$, or C(CH$_3$)$_3$;
R$_1$=H, COOCH$_3$, COOR$_4$, COR$_4$, CH$_2$OH, (CH$_2$)$_n$OH, (CH$_2$)$_n$OR$_4$, CR$_3$=NOR$_3$, CH=NR$_3$;
R$_2$=H, OH, OCOR$_4$;
R$_3$=H, CH$_3$, CH$_2$Ar, (CH$_2$)$_n$Ar, Ar, lower alkyl, lower alkenyl or lower alkynyl; CH$_2$CH=CHZ, (CH$_2$)$_n$OH, (CH$_2$)$_n$OR$_4$, CH=CHZ; CH$_2$J-Maleimide, CH$_2$JN-Maleimide where J =CH$_2$ or O;(CH$_2$)$_n$OCOCH$_3$; (CH$_2$)$_n$OCOCH$_2$OCH$_3$; (CH$_2$)$_n$-morpholine; (CH$_2$)$_n$-piperidine; (CH$_2$)$_n$-piperazine;
R$_4$=CH$_3$, CH$_2$CH$_3$, alkyl, alkenyl, alkynyl, allyl, isopropyl, isobutyl;
R$_9$=H, COOCH$_3$, COOR$_4$, COR$_4$, CH$_2$OH, (CH$_2$)$_n$OH, (OH$_2$)$_n$OR$_4$;
n =0-4;
m =0-4;
Z =F, Cl, I or Br; and
b) a linker-acceptor moiety connected to the ligand, comprising
1) an acceptor moiety that covalently binds the transporter or receptor; and
2) a linker which attaches the ligand to the acceptor moiety, the linker comprising a —CH$_2$— moiety attached to X; wherein the Linker is selected from—(CH$_2$)$_n$O(CH$_2$)$_m$—,—(CH$_2$)$_n$OCO (CH$_2$)$_m$—,—(CH$_2$)$_n$COO(CH$_2$)$_m$—, or—(CH$_2$)$_n$S (CH$_2$)$_m$—, wherein n =1-4 and m =0-4; and wherein the linker comprises a cleavable bond, cleavage of which produces at least two components, (1) a barb comprising the acceptor moiety and (2) the ligand, wherein the ligand is released from the compound.

2. The compound of claim 1 wherein the acceptor moiety is a radical acceptor.

3. The compound of claim 1 wherein the acceptor moiety is an epoxide.

4. The compound of claim 1 wherein the acceptor moiety is an alkenyl moiety.

5. The compound of claim 1 wherein the ligand is a tropane and the monoamine transporter is the dopamine transporter.

6. The compound of claim 1 wherein the ligand is a tropane moiety and the monoamine transporter is the serotonin transporter.

7. The compound of claim 1 wherein the acceptor moiety inhibits binding of cocaine at a monoamine transporter or receptor.

8. The compound of claim 1 wherein the compound inhibits binding of cocaine at a muscarinic cholinergic receptor.

9. The compound of claim 7 or 8 wherein the ligand has an Ic$_{50}$ of less than 500 nM with respect to [$^3$H]CFT inhibition of DAT.

10. The compound of claim 1 wherein the monoamine transporter is DAT.

11. The compound of claim 10 wherein binding of the acceptor moiety to the monoamine transporter allows DA transport.

12. The compound of claim 1 where the linker-acceptor moiety is selected from the following: (CH$_2$)$_n$ OCH$_2$CH=CH$_2$; (CH$_2$)$_n$D(CH$_2$)$_m$CH=CH$_2$; (CH$_2$)$_n$ SCH$_2$CH=CH$_2$; (CH$_2$)$_n$OCH$_2$(CH$_2$)$_n$CH=CH$_2$; (CH$_2$)$_n$ OCO(CH$_2$)$_m$CH=CH$_2$; (CH$_2$)$_n$OCO(CH$_2$)$_m$CH—(O : epoxide)-CH$_2$; (CH$_2$)$_n$OCO(CH$_2$)$_m$CH$_3$; (CH$_2$)$_n$OCO (CH$_2$)$_m$ OCH$_3$; (CH$_2$)$_n$OCOCH(CH$_3$)$_3$; (CH$_2$)$_n$OCO(CH$_2$)$_m$ CH(CH$_3$)$_2$; (CH$_2$)$_n$OCO(CH$_2$)$_m$CH$_3$; (CH$_2$)$_n$OCOCH$_2$CH (R$_2$)$_2$; (CH$_2$)$_n$OCOCHR$_4$CH(R$_2$)$_2$; (CH$_2$)$_n$OCOCHCHR$_2$;( CH$_2$)$_n$OCHCH(R$_2$)$_2$ ; (CH$_2$)$_n$OCOCH$_3$; (CH$_2$)$_n$ OCOCH$_2$OCH$_3$;

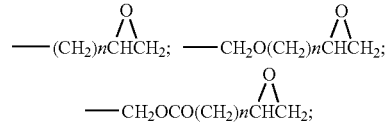

where D =O or S; J=CH$_2$ or O; n=0-4; m=0-4; and p=0-3.

13. The compound of claim 1, wherein the Acceptor is selected from the following structures:

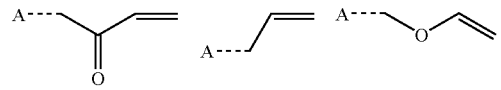

-continued

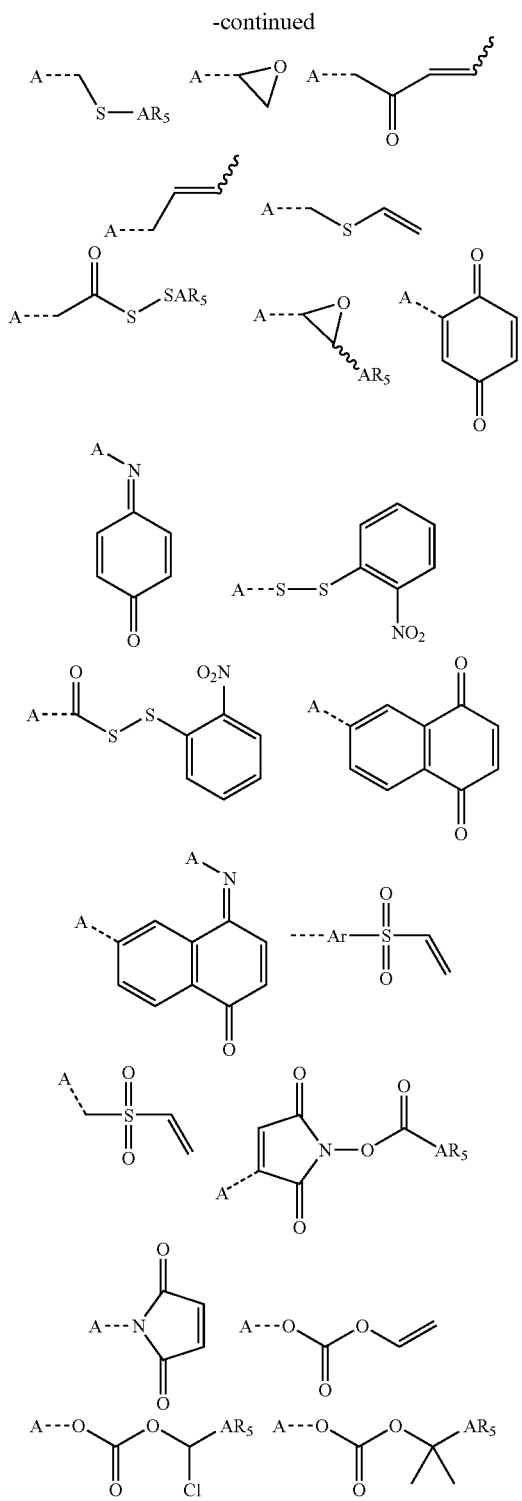

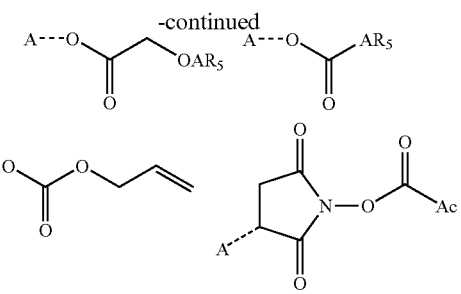

where A is —(CH$_2$)$_n$-D-(CH$_2$)$_m$—;
D =CH$_2$, (CH$_2$)$_p$,O, S, NH, SO and SO$_2$;
R$_5$ is H, CH$_3$,(CH$_3$)$_2$, (CH$_2$)$_n$SO$_3$Q, alkyl, (alkyl)$_2$, alkenyl, alkynyl, Ar, F, Cl, OCH$_3$ and
Q=K$^+$, Na$^+$, Li$^+$, Ca$^{2+}$, NH$_4^+$, RNH$_3^+$, or other pharmaceutically acceptable salts.

14. The compound of claim 1, wherein the Acceptor is selected from the following structures: —CH$_2$CH═CH$_2$;

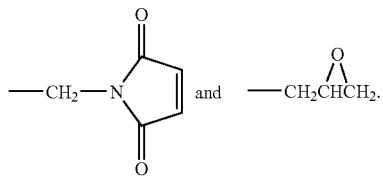

15. The compound of claim 1 wherein X is O.
16. The compound of claim 1 wherein R$_2$ is H.
17. The compound of claim 1 wherein Ar is phenyl substituted with substituents selected from: one or more —Cl, one or more —F, and a combination of —Cl and —F.
18. The compound according to claim 1, wherein the linker-accertor comprises a moiety selected from the group consisting of: —(CH$_2$)$_n$CH═CH$_2$; —CH$_2$O(CH$_2$)$_n$CH═CH$_2$, —CH$_2$OCO(CH$_2$)$_n$CH═CH$_2$;

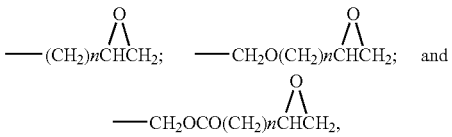

where n =1-4.
19. A pharmaceutical composition comprising a compound according to claim 1, together with a pharmaceutically acceptable carrier.
20. A method of inhibiting binding of cocaine to the DAT comprising administering an effective amount of a compound according to claim 1, wherein the transport of dopamine is not completely inhibited.

* * * * *